(12) United States Patent
Matsuzawa et al.

(10) Patent No.: US 7,153,259 B2
(45) Date of Patent: Dec. 26, 2006

(54) CAPSULE TYPE ENDOSCOPE

(75) Inventors: Hirohiko Matsuzawa, Hachioji (JP); Takeshi Yokoi, Hino (JP); Tatsuya Orihara, Hachioji (JP); Mitsujiro Konno, Hino (JP)

(73) Assignee: Olympus Corporation, Tokyo (JP)

( * ) Notice: Subject to any disclaimer, the term of this patent is extended or adjusted under 35 U.S.C. 154(b) by 206 days.

(21) Appl. No.: 10/929,477

(22) Filed: Aug. 31, 2004

(65) Prior Publication Data

US 2005/0124858 A1 Jun. 9, 2005

(30) Foreign Application Priority Data

| Sep. 1, 2003 | (JP) | ............................. 2003-309342 |
| Sep. 4, 2003 | (JP) | ............................. 2003-313188 |
| Aug. 27, 2004 | (JP) | ............................. 2004-247853 |

(51) Int. Cl.
*A61B 1/06* (2006.01)
*A61B 1/00* (2006.01)

(52) U.S. Cl. ....................... 600/160; 600/101
(58) Field of Classification Search ................ 600/101, 600/103, 117, 118, 160
See application file for complete search history.

(56) References Cited

FOREIGN PATENT DOCUMENTS

| JP | 04-327624 | 5/1994 |
| JP | 09-055440 | 9/1998 |
| JP | 10-370328 | 7/2000 |

Primary Examiner—John Leubecker
Assistant Examiner—Philip R Smith
(74) Attorney, Agent, or Firm—Kenyon & Kenyon LLP

(57) ABSTRACT

A capsule type endoscope includes an illumination device, an imaging device, and a transparent cover covering the illumination device and the imaging device. The imaging device has an objective optical system and an image sensor. When the objective optical system satisfies Condition (1) described below and a white cylinder with a reflectance of 90%, satisfying Condition (3) described below, is observed, illuminance of the imaging surface of the image sensor satisfies Condition (2) described below, in a state where a longitudinal center axis of a capsule coincides with the center axis of the white cylinder with a reflectance of 90%.

$$\omega \geq 50° \quad (1)$$

$$T_1 \times 0.5 \leq T_2 \quad (2)$$

$$D = 1.2 \times \Phi \quad (3)$$

where $\omega$ is a half of a field angle of the objective optical system, $T_1$ is the maximum illuminance in an area on the imaging surface of the image sensor corresponding to a field region of the objective optical system, $T_2$ is illuminance at a position on the imaging surface of the image sensor corresponding to a half of the maximum image height of the objective optical system, D is the inside diameter of the white cylinder, and $\Phi$ is the outside diameter of the capsule type endoscope.

6 Claims, 41 Drawing Sheets

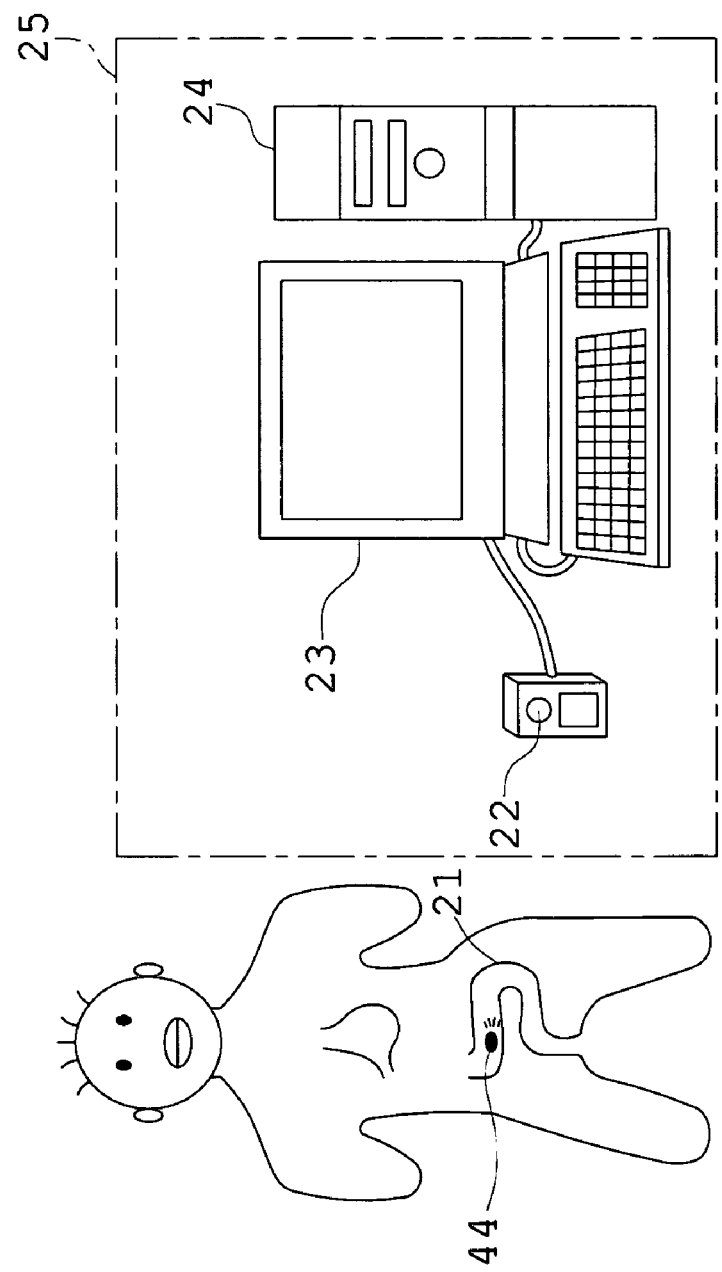

STATE WHERE LONGITUDINAL CENTER AXIS OF CAPSULE COINCIDES WITH CENTER AXIS OF TUBULAR STRUCTURE

OPTICAL AXIS OF IMAGING OPTICAL SYSTEM

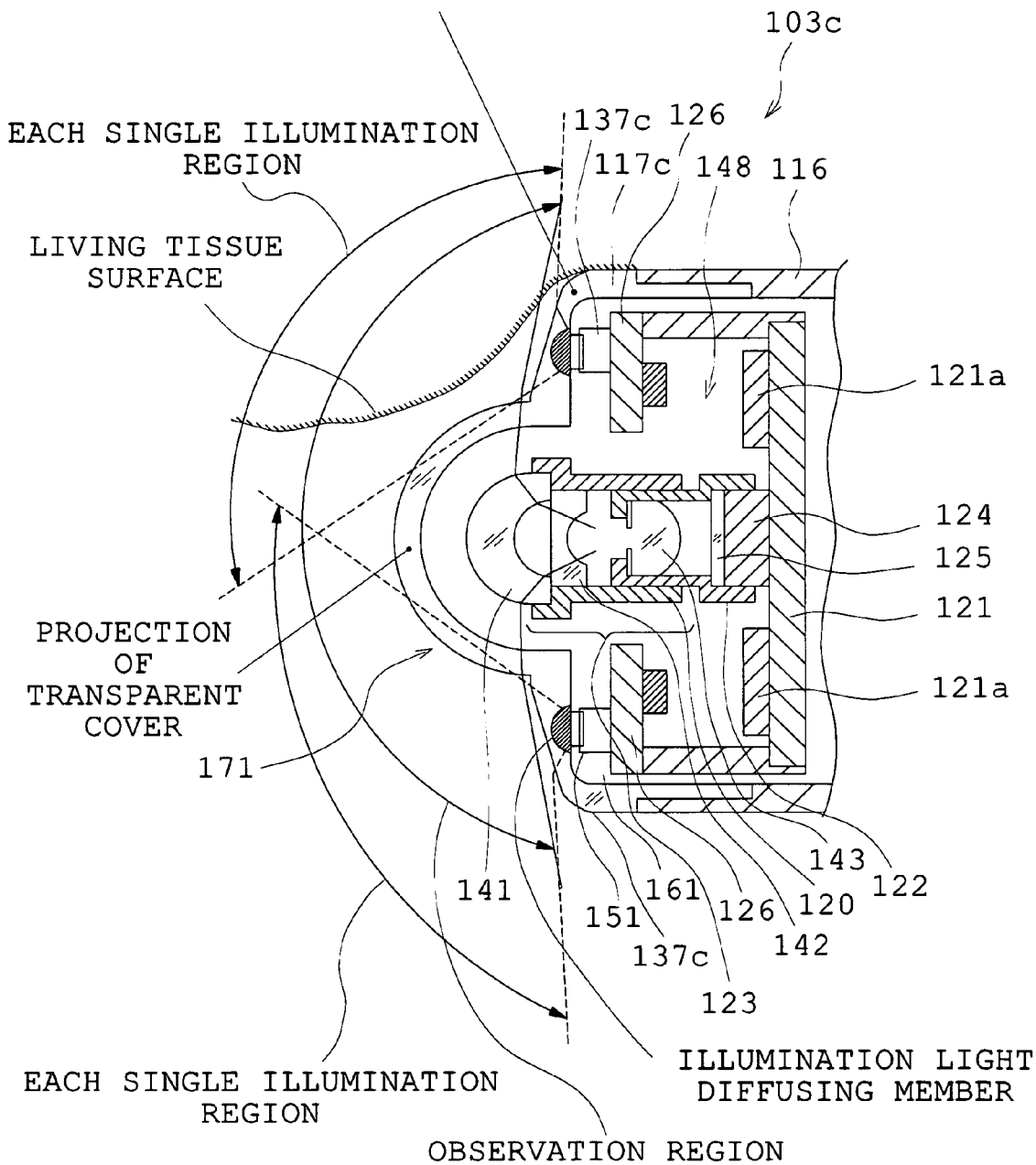

209

209

209

209

CAPSULE TYPE ENDOSCOPE

The contents of application Ser. No. 2003-309342 filed on Sep. 1, 2003; 2003-313188 filed on Sep. 4, 2003; and 2004-247853 filed on Aug. 27, 2004, in Japan, are incorporated by this reference.

BACKGROUND OF THE INVENTION

1. Field of the Invention

This invention relates to a capsule type endoscope, and in particular, to a capsule type endoscope used to examine the part of a cylindrical structure such as the small intestine.

2. Description of Related Art

Recently, in endoscopy, capsule type endoscopes have come to be used in the field of medicine. Such an endoscope does not require an insertion tube, is provided with a transparent cover at its distal end, and is configured into a capsule shape so that when a patient swallows the capsule type endoscope, pain that formerly has been experienced by the insertion of the insertion tube section can be relieved.

In a common endoscope, for example, in order to form images inside the stomach in a wide range and to search a lesion, an illumination optical system is constructed so that the region of a visual field to be imaged is made wide as far as possible, an illumination region of illumination light illuminating this region to be imaged is made large as far as possible, and the illuminance of the entire imaging area becomes uniform. Such wide-angle illumination optical systems are disclosed, for example, in Japanese Patent Kokai Nos. Hei 10-239586, Hei 6-148519, and 2000-193894.

In order to find the lesion as easily as possible, a capsule type endoscope that, in addition to a function of carrying out an ordinary observation through a color image, for example, is capable of irradiating a living tissue with excitation light to observe fluorescence from the living tissue is proposed. Such a capsule type endoscope is disclosed, for example, in PCT WO 02/36007. An example of a technique for making observations on both an ordinary color image and a particular image represented by a fluorescent image is disclosed in PCT WO 03/11103.

In one of the observations of the particular image used together with the ordinary color image in order to find the lesion as easily as possible, there is a technique referred to as narrow band imaging (hereinafter abbreviated to NBI) in which the living tissue is irradiated with narrow-band light and reflected light from the living tissue is imaged and observed. Its feature is as described below. For example, short-wavelength light, such as blue light, has a small penetration depth into a living body. Consequently, when short-wavelength, narrow-band light is used in the NBI, this short-wavelength light, containing only information about the surface of the living tissue, is reflected, and thus an observation image specializing the surface of the living tissue can be obtained. On the other hand, when light of a large penetration depth into the living body, such as red light, is used in the NBI, this long-wavelength light, containing information on the deep part of the living tissue, is reflected, and thus a state of the deep part of the living tissue can be imaged. In the NBI, for example, it is possible to clearly depict the capillary of the surface of a mucous membrane without spraying pigment on the surface of the living body or injecting a contrast medium, such as indocyanine green (ICG), around a tumor produced in the living tissue. Thus, in the capsule type endoscope, a combination of the observation of the ordinary color image with the NBI contributes to the improvements of accuracy of the detection of Barrett's esophagus and glandular cancer in early stages; the identification of differentiation, an invasion area, and a penetration depth of cancer detected at early stages; assistance to a pit pattern diagnosis of the tumor of the large intestine; and a stage diagnosis of a inflammatory intestinal disease. When the NBI is combined with a high-magnification endoscopic observation, a further effect is brought about.

SUMMARY OF THE INVENTION

The capsule type endoscope according to the present invention comprises an illumination means for illuminating an object, an imaging means for imaging the object, and a transparent cover for covering the illumination means and the imaging means. The imaging means includes an objective optical system and an image sensor. When the objective optical system satisfies Condition (1) described below and a white cylinder with a reflectance of 90%, satisfying Condition (3) described below, is observed, illuminance of the imaging surface of the image sensor satisfies Condition (2) described below, in a state where a longitudinal center axis of a capsule coincides with the center axis of the white cylinder with a reflectance of 90%.

$$\omega \geq 50° \tag{1}$$

$$T_1 \times 0.5 \leq T_2 \tag{2}$$

$$D = 1.2 \times \Phi \tag{3}$$

where $\omega$ is a half of a field angle of the objective optical system, $T_1$ is the maximum illuminance in an area on the imaging surface of the image sensor corresponding to a field region of the objective optical system, $T_2$ is illuminance at a position on the imaging surface of the image sensor corresponding to a half of the maximum image height of the objective optical system, D is the inside diameter of the white cylinder, and $\Phi$ is the outside diameter of the capsule type endoscope.

In the capsule type endoscope of the present invention, it is desirable that the objective optical system is constructed so that when a uniform surface illuminant is observed, the illuminance of the imaging surface of the image sensor at the half of the maximum image height is less than 50% of the maximum illuminance of the imaging surface of the image sensor within the field region.

In the capsule type endoscope of the present invention, it is desirable that the objective optical system includes at least one aspherical lens.

In the capsule type endoscope of the present invention, it is desirable that the objective optical system has a light-blocking member cutting off marginal rays.

In the capsule type endoscope of the present invention, it is desirable that the illumination means is constructed with a plurality of LEDs arranged so that their center axes are inclined with respect to the optical axis of the objective optical system.

In the capsule type endoscope of the present invention, it is desirable that an illumination distribution of the surface of a spherical object placed ahead of the objective optical system satisfies the following condition:

$$R(\theta) \leq R(O) \times \cos^2(\theta) \tag{4}$$

where $R(\theta)$ is illuminance of an object surface relative to a field angle $\theta°$ C. of the objective optical system and $R(O)$ is illuminance of the object surface crossing the optical axis of the objective optical system.

These and other features and advantages of the present invention will become apparent from the following detailed description of the preferred embodiments when taken in conjunction with the accompanying drawings.

BRIEF DESCRIPTION OF THE DRAWINGS

FIG. 2 is a conceptual view showing the construction of a capsule type endoscope system displaying an image, using the capsule type endoscope of the first embodiment;

FIG. 27 is an enlarged sectional view showing the distal end of the capsule type endoscope of a sixth embodiment in the present invention;

DETAILED DESCRIPTION OF THE PREFERRED EMBODIMENTS

Figure 1A:
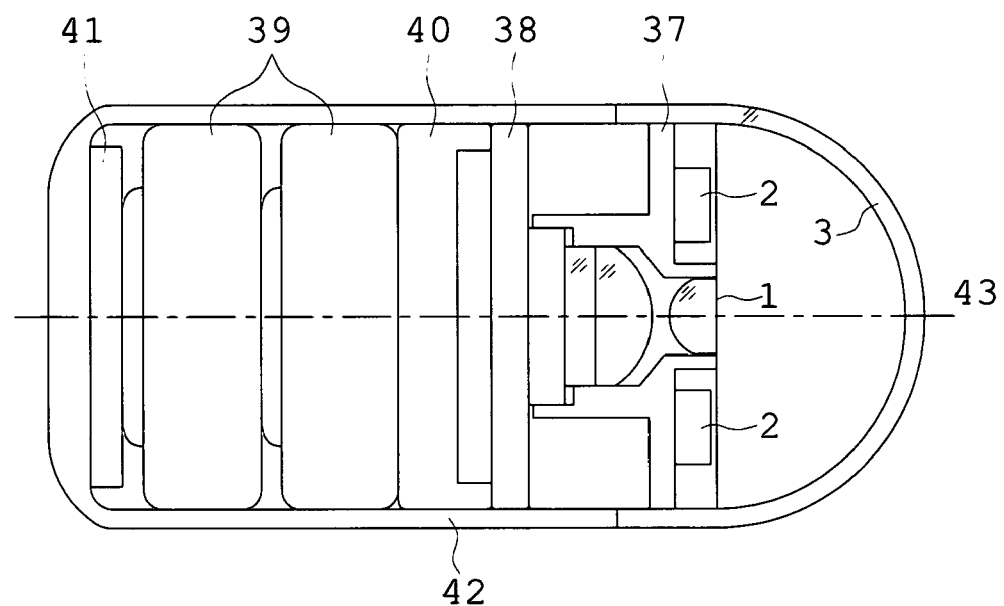
FIG. 1A is a sectional view showing schematically the structure, exhibited along the optical axis, of the capsule type endoscope of a first embodiment in the present invention.

Before undertaking the description of the embodiments, the function and effect of the present invention will be explained.

When the objective optical system, as in the capsule type endoscope of the present invention, is constructed so that the objective optical system satisfies Condition (1) and the white cylinder with a reflectance of 90%, satisfying Condition (3), is observed, the illuminance of the imaging surface of the image sensor satisfies Condition (2) in a state where the longitudinal center axis of the capsule coincides with the center axis of the white cylinder with a reflectance of 90%, a favorable brightness distribution can be obtained even in the case where the part of the cylindrical structure, such as the small intestine, is observed and examined.

The capsule type endoscope according to the present invention is assumed as the one mounting an imaging optical system that has a wide field angle. Thus, it is necessary that the half field angle ω satisfies Condition (1).

If Condition (1) is not satisfied and ω<50°, the field region will be narrowed when the part of the inner wall of a tubular organ, such as the small intestine, is examined. This constitutes an obstacle to the observation and examination. Condition (1) is satisfied and thereby a good field region is obtained without offering any obstacle against the observation and examination.

It is desirable to satisfy a condition, ω≧60°, because even when the living tissue has a fold-shaped, rough structure, the observation and examination can be carried out without missing a portion casting the shadow of the fold.

Condition (2) in the capsule type endoscope of the present invention is provided to obtain a good brightness distribution in the whole range of the visual field without producing halation on an image periphery with respect to the capsule type endoscope of the wide field angle mentioned above.

In the observation carried out by using the capsule type endoscope, a state of the production of halation depends on the reflectance of the living body and the positional relationship between the object and the capsule, but when the object is made close to the capsule in the visual field of the objective optical system, the halation is liable to occur. Such states are roughly divided into the following two cases. One of them is a case where the inner wall of the tubular organ comes in close contact with the periphery of the capsule. Tubular organs, such as esophagus and intestines, make up 80% of the alimentary canal that is a chief observation object of the capsule type endoscope. Where air is not fed into these organs, the organs contract so that tubes are practically blocked by inner walls. Consequently, the capsule often comes in close contact with the inner wall of the tubular organ, and a distance between the capsule and the object is reduced so that the halation is liable to occur on the periphery of the visual field of the objective optical system. Illumination light emitted from the illumination means, after being reflected by the object, is incident on the objective optical system and is collected on the light-receiving surface of the image sensor to form the illuminance distribution in an effective imaging range of the light-receiving surface. In this case, illuminance of a portion corresponding to the periphery of the visual field on the light-receiving surface exceeds an allowable intensity of the image sensor, and in the entire peripheral area of an image displayed on a display device such as a monitor, the image cannot be normally reproduced. The other is a case where a part of the periphery of the capsule comes in close contact with the inner wall of the organ that has a relatively wide space, such as the stomach. In this case, on one side of the visual field, a distance between the objective optical system and the object is diminished, while on the opposite side thereof, the distance is increased. Hence, the halation is produced on a part of the periphery of the image. In either case, the illuminance of the light-receiving surface of the image sensor is unevenly distributed on the periphery of the visual field. In such a state, the halation is liable to be produced.

When the imaging optical system of the wide field angle is used to image the interior of the tubular space, the density of the image ranging from the middle of the visual field to the periphery appears to be higher than that of the image ranging from the center of the visual image to the middle. This is characteristic of aberration produced in the objective optical system of the wide field angle and becomes pronounced as an image height on the imaging surface exceeds ½ and approaches its maximum. Thus, for example, when the imaging optical system mentioned above is used to image a light source that has a uniform luminance distribution and is equidistant from the range from the center of the visual field to the periphery, the illuminance of the light-receiving surface of the image sensor becomes progressively high in going from the center of the visual field to the periphery. In a tubular object, since the distance between the imaging optical system and the object is diminished in going to the periphery of the visual field, unevenness of the illuminance distribution of the light-receiving surface of the image sensor becomes pronounced on the periphery of the visual field and the halation is liable to be produced.

Here, in the present invention, in order to reproduce an observation state of the tubular organ described above, a cylindrical fixture with proper reflectance is provided in the inner wall and is fixed so that the center axis of the cylinder coincides with the longitudinal center axis of the capsule. In this case, the inside diameter D of the cylinder is found by the outside diameter Φ, the reflectance of the living tissue, and the reflectance of the inner wall of the cylinder. For example, in the case where the inner wall, like that of the small intestine, is constructed with a myriad of projection tissues and in addition, its surface is covered with mucus, the reflectance by the living tissue is seriously affected by the attenuation of light due to absorption and scattering on a tissue surface. Furthermore, in the observation of the tubular organ by the capsule type endoscope, there is the need to consider the distribution of light of the illumination means and an angle of incidence of illumination light on the living tissue. When the amount of light incident on the tissue surface is assumed as 1, the amount of light reflected by the living tissue and incident on the imaging optical system is reduced to approximately 0.4. In the present invention, therefore, the reflectance of the living tissue is assumed as 40%. In this case, the inside diameter of the white cylinder that has the inner wall with a preset reflectance relative to white light is found by the following equation:

$$(0.025 \times \alpha)^{1/4} \times \Phi = D \quad (6)$$

where $\alpha$ is the reflectance (%) of the inner wall of the white cylinder, D is the inside diameter (mm) of the white cylinder, and $\Phi$ is the outside diameter (mm) of the capsule type endoscope.

For example, when the inner wall of the cylinder is designed to have a reflectance of 90% relative to white light, the inside diameter D of the cylinder is expressed like Condition (3). With the capsule type endoscope fixed to the cylindrical fixture, the inner wall of the cylinder is illuminated by the illumination means of the capsule type endoscope and the inner wall of the cylinder is imaged by an imaging optical system of a wider field angle. In this case, the illuminance of the light-receiving surface of the image sensor is distributed so as to satisfy Condition (2), and thereby the capsule type endoscope in which halation on the periphery of the image is not produced and the visual field can be observed with good brightness can be realized.

In the capsule type endoscope, an imaging signal from the image sensor is transmitted to an image processing circuit by a radio device through a receiving device located away from the capsule, and after being transformed into an image signal, is displayed as an image on the display device such as the monitor. In the manufacturing process of the capsule type endoscope, therefore, when whether the illuminance distribution of the light-receiving surface of the image sensor satisfies Condition (2) is examined, the intensity of the image signal output to the display device is measured in the range from the center of the image to the periphery and the intensity distribution of the image signal is depicted to determine whether the following condition is satisfied from the profile of the intensity distribution. Whereby, equivalent evaluation is possible.

$$T_3 \times 0.5 \leq T_4 \quad (5)$$

where $T_3$ is the maximum value of the intensity of the image signal measured in the range from the center of the image to the periphery and $T_4$ is the value of the intensity of the image signal corresponding to a half of the field angle of the objective optical system.

Figure 18:
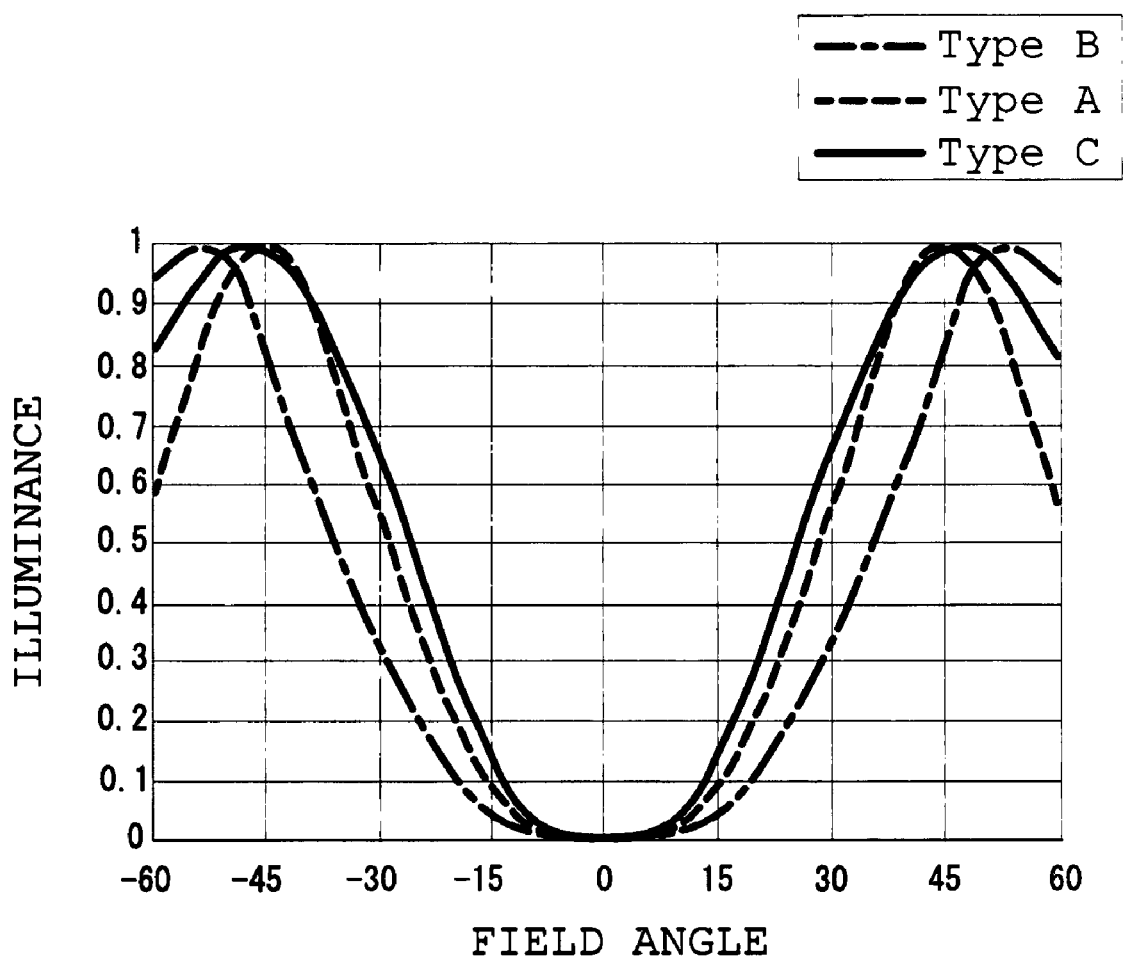
FIG. 18 is a graph conceptually showing the illuminance of the imaging surface when the white cylinder is imaged, plotted against the field angle of the objective optical system.

FIG. 18 shows the illuminance of the imaging surface when the white cylinder is imaged, plotted against the field angle. In this figure, Type A indicates an example of an ordinary endoscope optical system, and Types B and C indicate examples of optical systems in which the capsule type endoscope of the present invention is used.

In the observation of the cylindrical object, when the field angle becomes wide, a distance to the object to be observed is reduced and thus the intensity of reflected light from the object is increased. Hence, at a wide field angle, when the illuminance of the light-receiving surface of the image sensor is set so as to lower on the periphery of the visual field, the brightness of the image becomes uniform, which is favorable for observations and diagnoses. Specifically, when the illuminance distribution of the light-receiving surface of the image sensor is normalized by the maximum value of the illuminance, the illuminance at the position of the light-receiving surface corresponding to a half of the maximum image height is set so as to increase, and thereby the illuminance of the image at the maximum height can be lowered.

In Type A, the image illuminance is high on the periphery of the visual field and the illuminance of the light-receiving surface corresponding to a half of the maximum image height is as low as about 0.3. Consequently, halation is produced on the periphery of the visual field, and the center and the vicinity thereof become dark.

In Type B or C, besides the fact that the illuminance of the light-receiving surface on the periphery of the visual field is high, the image illuminance corresponding to a half of the maximum image height is as high as about 0.51 or 0.65. In the capsule type endoscope, therefore, halation is not produced on the periphery of the visual field and a good image can be obtained in the whole range of the visual field.

Also, a difference between Type B and Type C is that Type B fulfils Condition (2) by considering the placement of a field stop of the imaging optical system, while Type C satisfies Condition (2) by controlling distortion in the imaging optical system.

In the capsule type endoscope of the present invention, it is desirable to satisfy a condition, $T_1 \times 0.6 \leq T_2$, well over Condition (2), because the brightness distribution of the center and periphery of the image becomes favorable and the observation and examination of the cylindrical structure are facilitated.

In the capsule type endoscope of the present invention, it is desirable that the amount of production of distortion in the imaging optical system is controlled as a standard so that the illuminance of the light-receiving surface of the image sensor corresponding to a half of the maximum image height in imaging a uniform surface illuminant is less than 50% of the maximum illuminance of the imaging surface of the image sensor within the field region. By setting the amount of production of distortion in the imaging optical system as mentioned above, it is possible to construct the imaging optical system suitable for the capsule type endoscope in which halation is not produced on the periphery of the visual field and a good image can be obtained in the whole range of the visual field.

At least one of surfaces of lenses constituting the imaging optical system is configured as an aspherical surface, and thereby the effect that the amount of production of distortion can be easily controlled is brought about. Furthermore, since the focal length of the imaging optical system is reduced and the depth of field can be increased, the imaging optical system in which an enlargement observation of the object is also possible can be constructed.

Instead of controlling distortion in the imaging optical system, a light beam passing through the imaging optical system and imaged on the periphery of the visual field is controlled by the field stop. Whereby, the illuminance of the light-receiving surface of the image sensor can also be adjusted so that it is properly distributed. With the image of the inner wall of the tubular object formed by the imaging optical system in which the amount of production of distortion is controlled, accommodation relative to the middle and periphery of the visual field may be impaired. According to the aspect of the present invention, however, it is possible to construct the capsule type endoscope in which natural accommodation is obtained, halation is not produced on the periphery of the visual field, and a good image can be secured in the whole range of the visual field. In addition, since the field stop blocks marginal rays to adjust the brightness of the periphery, there is no need to make a complicated lens arrangement for controlling the amount of marginal light, and lens fabrication can be facilitated. Even when an ND filter designed to attenuate the intensity of the light beam on the periphery of the visual field is placed instead of the field stop, the same effect can be obtained.

Figure 20:
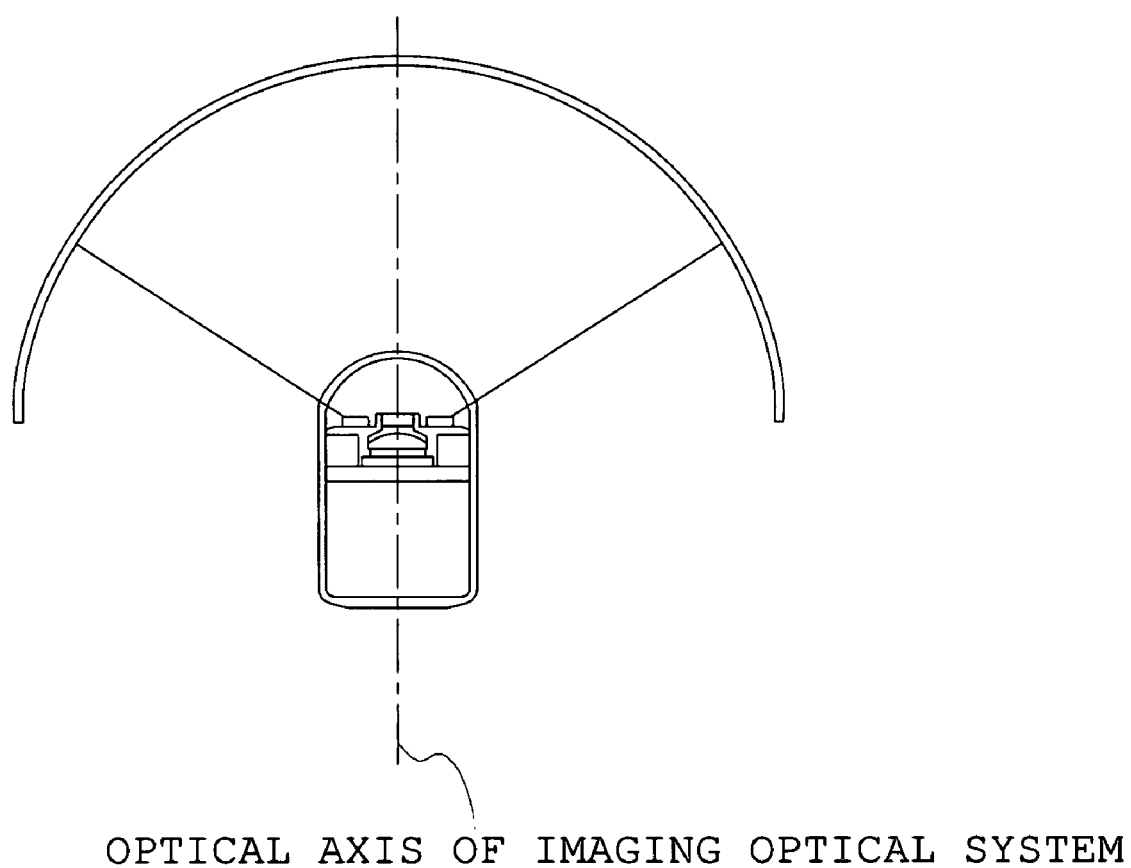
FIG. 20 is a view showing the positional relationship between the spherical object and the capsule type endoscope.

In the capsule type endoscope of the present invention, it is possible to prevent halation from occurring on the periphery of the visual field by considering the illumination means. Specifically, as shown in FIG. 20, when an object equidistant from the range from the center of the visual field to the periphery (which is thought of as spherical in shape at some distance away from the imaging optical system) in front of the imaging optical system is illuminated by the illumination means, the illuminance distribution of the object surface satisfies Condition (4), and thereby the illuminance of the object can be prevented from increasing on the periphery of the visual field of the imaging optical system.

Consequently, it is possible to construct the capsule type endoscope in which halation is not produced on the periphery of the visual field and a good image can be obtained in the whole range of the visual field.

Figure 26A:
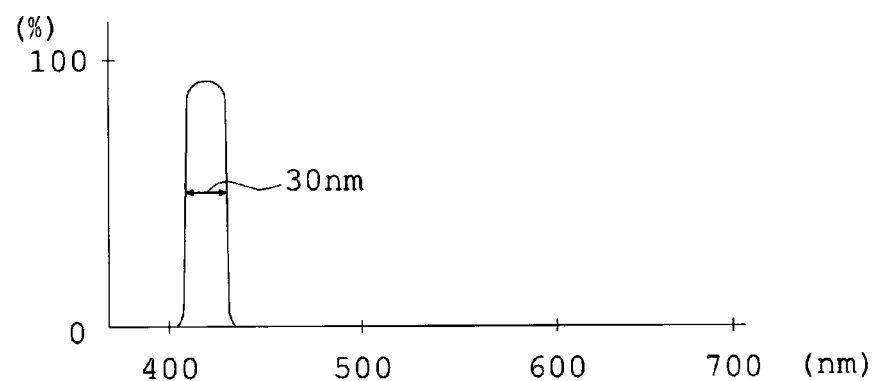
FIGS. 26A, 26B, and 26C are diagrams showing transmission characteristics of band-pass filters.
Figure 26B:
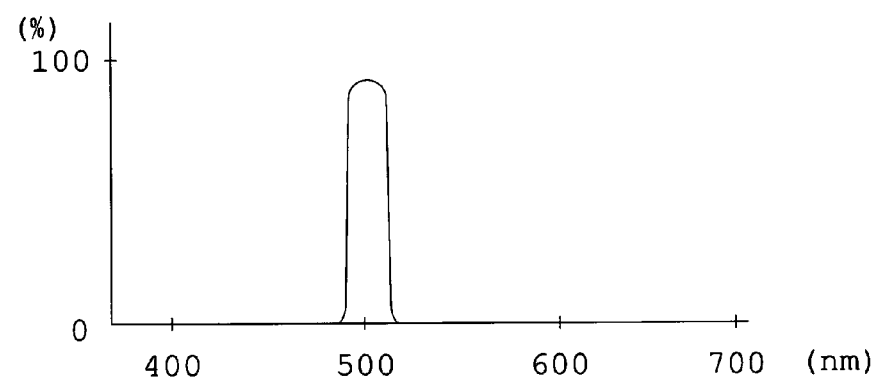
Figure 26C:
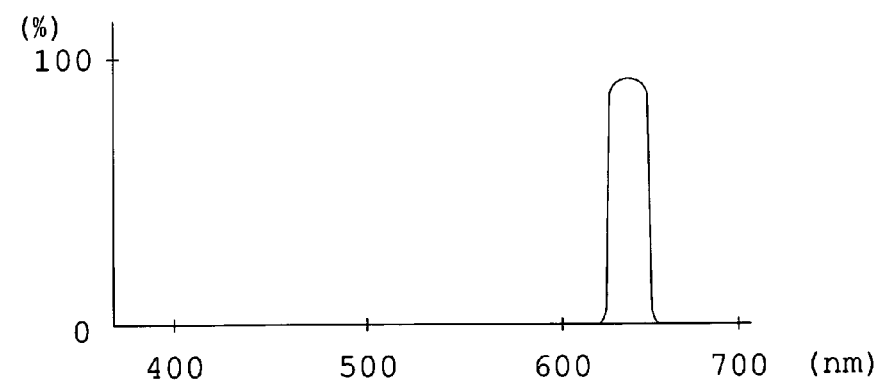

In a combination of the observation of the ordinary color image with the NBI, an illumination means producing white light and an illumination means producing the narrow-band light become necessary. In order to produce the narrow-band light, provision is made to place a band-pass filter in front of the light emergence surface of the illumination means producing white light or to use an element producing monochromatic light that has a narrow-band wavelength component, such as an LED or LD. FIGS. 26A, 26B, and 26C show examples of transmission characteristics of band-pass filters. It is desirable that the band width of illumination light used in the NBI is 30 nm or less in half-width. In the case where the living tissue is irradiated with such narrow-band light and reflected light from the living tissue is imaged, brightness is much lower than the case where white light is used for illumination. As such, in the capsule type endoscope in which two images, the ordinary color image and the NBI image, are formed by one imaging means, it is necessary to consider correction for the difference in brightness between the two images. When the light-receiving sensitivity of the image sensor is set to be suitable for forming the ordinary color image, it is desirable that the brightness ratio of each illumination means is adjusted so that the brightness of the NBI image is at least 20% of that of the ordinary color image. Thus, in the present invention, a cylindrical fixture with proper reflectance is provided in the inner wall, and the brightness is measured and adjustment is made, with the fixture fixed so that the center axis of the cylinder coincides with the longitudinal center axis of the capsule. In consideration of the attenuation of light due to absorption and scattering on the tissue surface and of the distribution of light of the illumination means and an angle at which illumination light is incident on the living tissue, when the amount of light incident on the tissue surface where the living tissue is irradiated with narrow-band light is assumes as 1, the amount of light reflected by the living tissue and incident on the imaging optical system is reduced to approximately 0.05. As such, the reflectance of the living tissue illuminated with the narrow-band light is assumed as 5%. In this case, the inside diameter D of the white cylinder that has the inner wall with a preset reflectance $\alpha$ relative to white light is found by the following equation:

$$(0.2\times\alpha)^{1/4}\times\Phi=D \tag{7}$$

For example, when the inner wall of the cylinder is designed to have a reflectance of 90% with respect to the white light, the inside diameter D of the cylinder is expressed as the following equation:

$$D=2\times\Phi \tag{8}$$

With the capsule type endoscope fixed to the cylindrical fixture, the inner wall of the cylinder is illuminated by the illumination means with narrow-band light provided in the capsule type endoscope, and the inner wall of the cylinder is imaged by the imaging optical system. Similarly, the inner wall of the cylinder is illuminated by the illumination means producing white light provided in the capsule type endoscope, and the inner wall of the cylinder is imaged by the imaging optical system. In this case, the capsule type endoscope that is capable of observing the two images, the ordinary color image and the NBI image, with favorable brightness when the illumination intensity of the narrow-band light is adjusted so that the maximum illuminance in the area of the imaging surface of the image sensor corresponding to the field region of the objective optical system satisfies the following condition:

$$T_c\times1.6\leq T_m \tag{9}$$

where $T_c$ is the maximum illuminance in the area of the imaging surface of the image sensor corresponding to the field region of the imaging means when the inner wall of the white cylinder is illuminated by the illumination means producing white light and $T_m$ is the maximum illuminance in the area of the imaging surface of the image sensor corresponding to the field region of the imaging means when the inner wall of the white cylinder is illuminated by the illumination means producing narrow-band light.

In the capsule type endoscope, the imaging signal from the image sensor is transmitted to the image processing circuit by the radio device through the receiving device located away from the capsule, and after being transformed into the image signal, is displayed as an image on the display device such as the monitor. In the manufacturing process of the capsule type endoscope, therefore, when whether the illuminance distribution of the light-receiving surface of the image sensor where the inner wall is illuminated by individual illumination means satisfies Condition (9) is examined, the intensities of the image signals output to the display device are measured in the range from the center of the image to the periphery and the values of the maximum intensities of the image signals are extracted to determine whether the following condition is satisfied. Whereby, equivalent evaluation is possible.

$$S_c\times1.6\leq S_m \tag{10}$$

where $S_c$ is the maximum value of the intensity of the image signal obtained through measurement ranging from the center of the image formed by the imaging means to the periphery where the inner wall of the white cylinder is illuminated by the illumination means producing white light and $S_m$ is the maximum value of the intensity of the image signal obtained through measurement ranging from the center of the image formed by the imaging means to the periphery where the inner wall of the white cylinder is illuminated by the illumination means producing narrow-band light.

In accordance with the drawing, the embodiments of the present invention will be explained below.

First Embodiment

Figure 1B:
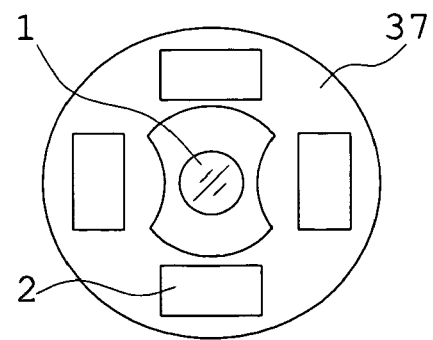
FIG. 1B is an explanatory view showing the arrangements of the objective optical system and the illumination optical system.

FIG. 1A shows the structure, exhibited along the optical axis, of the capsule type endoscope of the first embodiment in the present invention. FIG. 1B shows the arrangement of the objective optical system and the illumination optical system.

Figure 3:
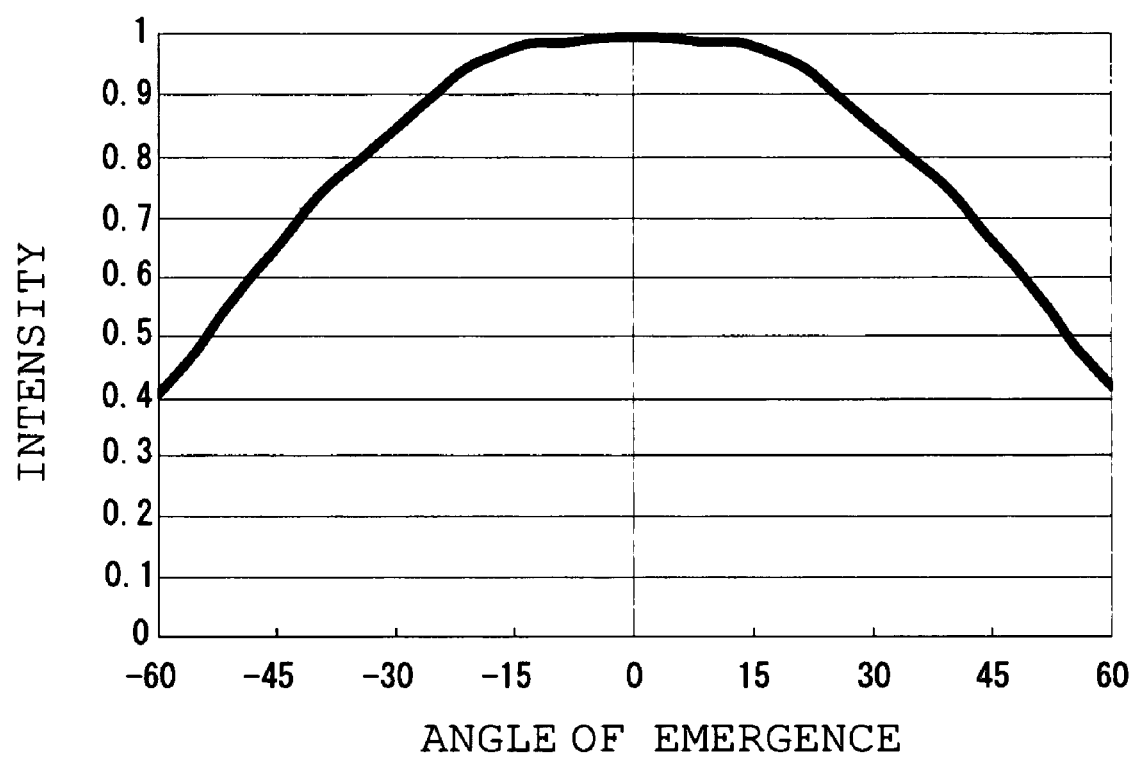
FIG. 3 is a graph showing the distribution of the intensity of illumination light plotted against an angle of emergence in the capsule type endoscope of the first embodiment.
Figure 4A:
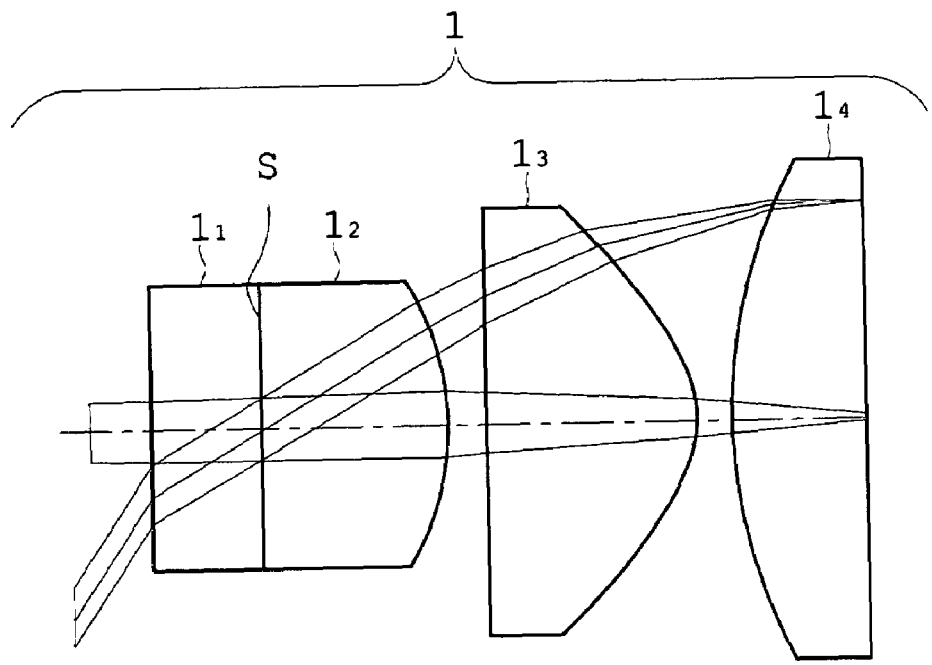
FIG. 4A is a sectional view showing the arrangement, developed along the optical axis, of the objective optical system in the capsule type endoscope of the first embodiment.
Figure 4B:
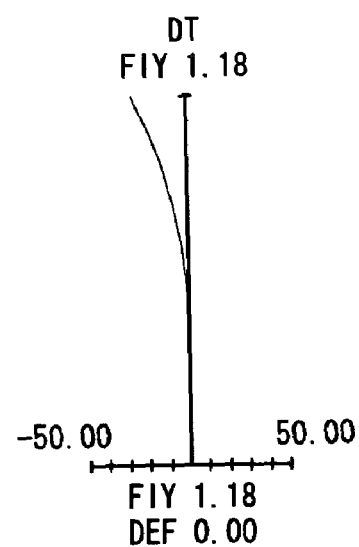
FIG. 4B is a diagram showing the aberration characteristic of distortion in the objective optical system.
Figure 5:
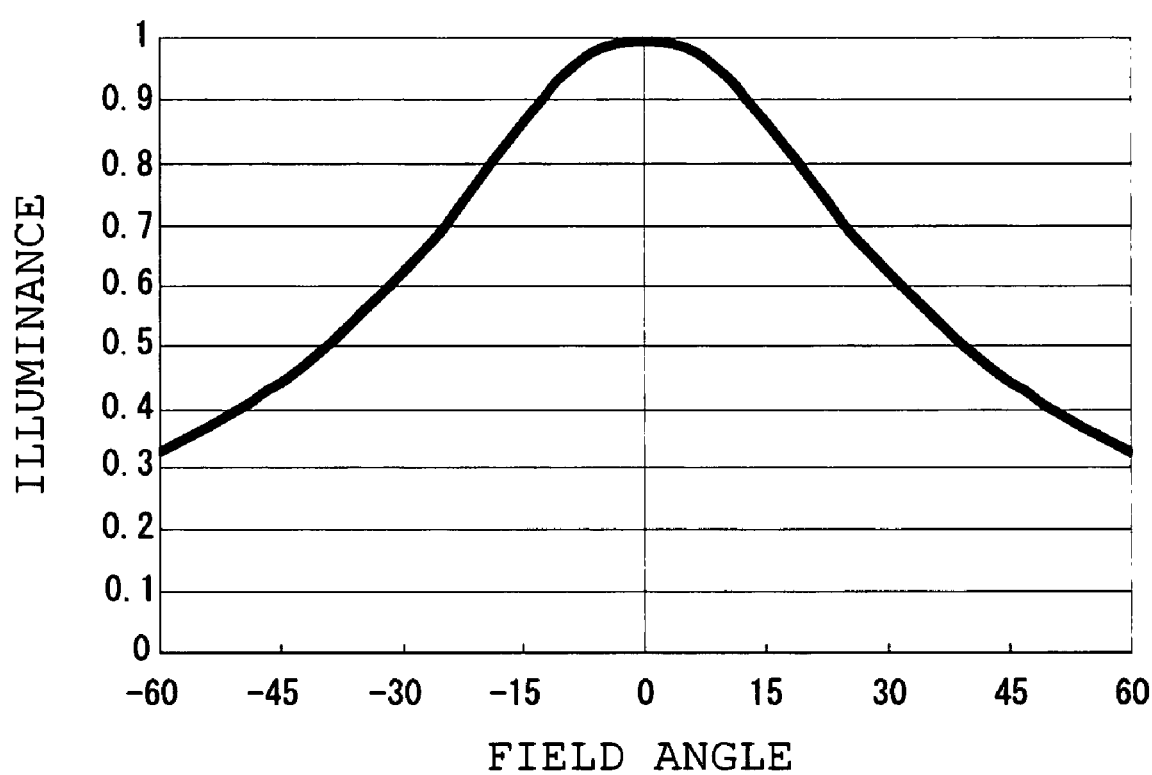
FIG. 5 is a graph showing the characteristic of illuminance plotted against the field angle of the objective optical system when a uniform surface illuminant is observed.
Figure 6:
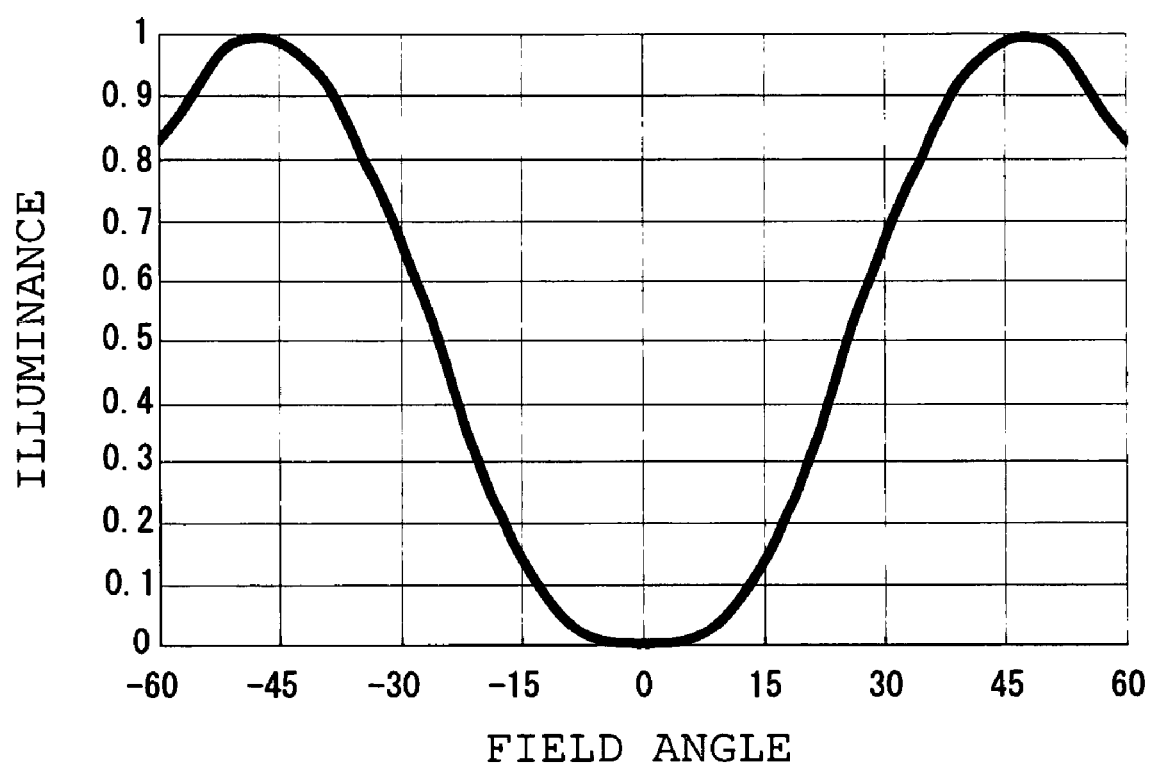
FIG. 6 is a graph showing the characteristic of illuminance of the surface of the image sensor plotted against the field angle of the objective optical system when the inner wall of the white cylinder is imaged in the capsule type endoscope of the first embodiment.
Figure 7:
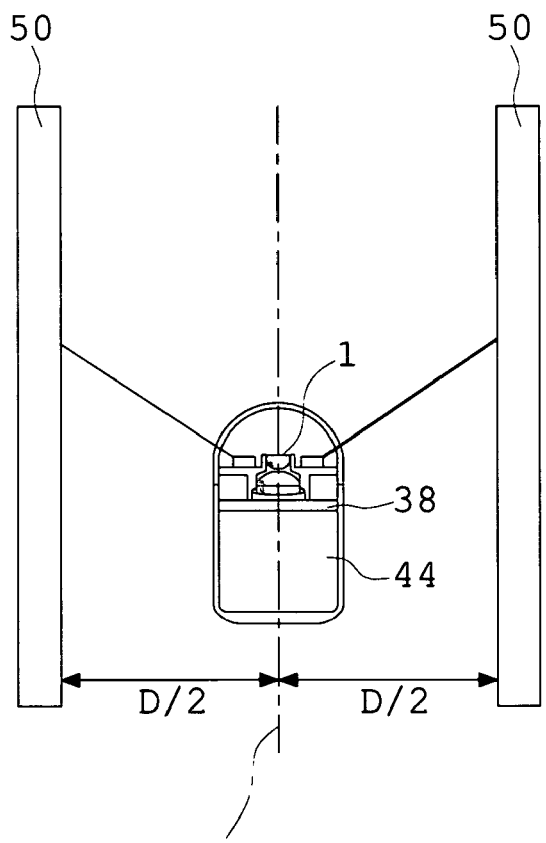
FIG. 7 is a schematic view showing a tubular structure used in the first embodiment in a state where the longitudinal center axis of the capsule coincides with the center axis of the tubular structure.

FIG. 2 shows the construction of a capsule type endoscope system displaying an image, using the capsule type endoscope of the first embodiment. FIG. 3 shows the distribution of the intensity of illumination light plotted against an angle of emergence in the capsule type endoscope of the first embodiment. FIG. 4A shows the arrangement, developed along the optical axis, of the objective optical system in the capsule type endoscope of the first embodiment. FIG. 4B shows the aberration characteristic of distortion in the objective optical system of FIG. 4A. FIG. 5 shows the characteristic of illuminance plotted against the field angle of the objective optical system when a uniform surface illuminant is observed. FIG. 6 shows the characteristic of illuminance of the surface of the image sensor plotted against the field angle of the objective optical system when the inner wall of the white cylinder is imaged in the capsule type endoscope of the first embodiment. FIG. 7 shows a tubular structure (the white cylinder) used in the first embodiment in a state where the longitudinal center axis of the capsule coincides with the center axis of the tubular structure (the white cylinder).

Figure 8A:
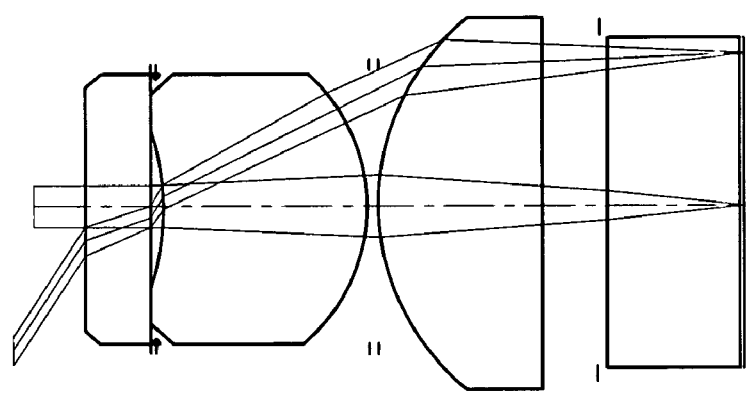
FIG. 8A is a sectional view showing the arrangement, developed along the optical axis, of an objective optical system used in a conventional endoscope.
Figure 8B:
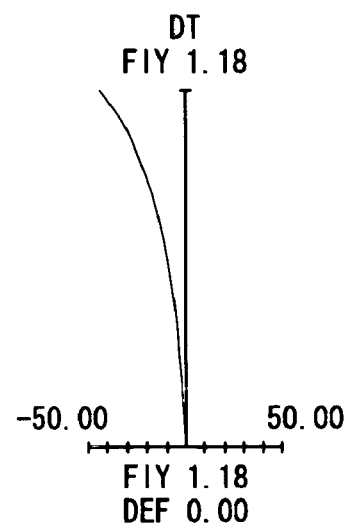
FIG. 8B is a diagram showing the aberration characteristic of distortion in the objective optical system.
Figure 9:
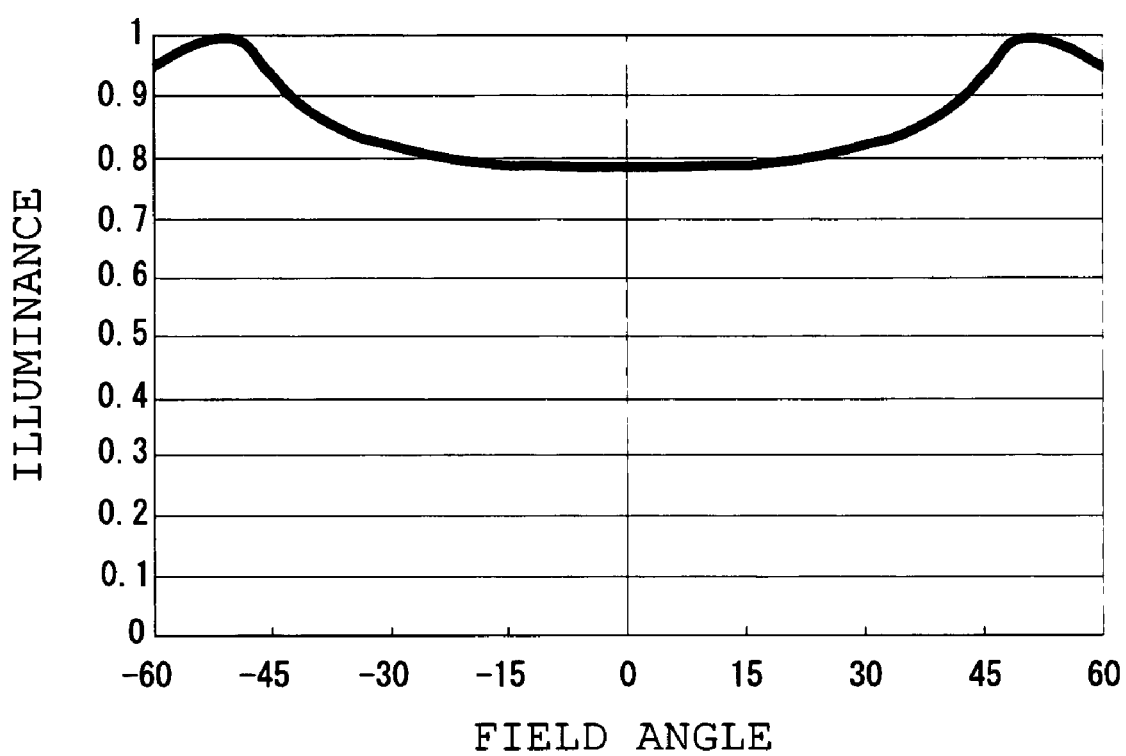
FIG. 9 is a graph showing the illuminance characteristic of the objective optical system of FIG. 8A when the uniform surface illuminant is observed.
Figure 10:
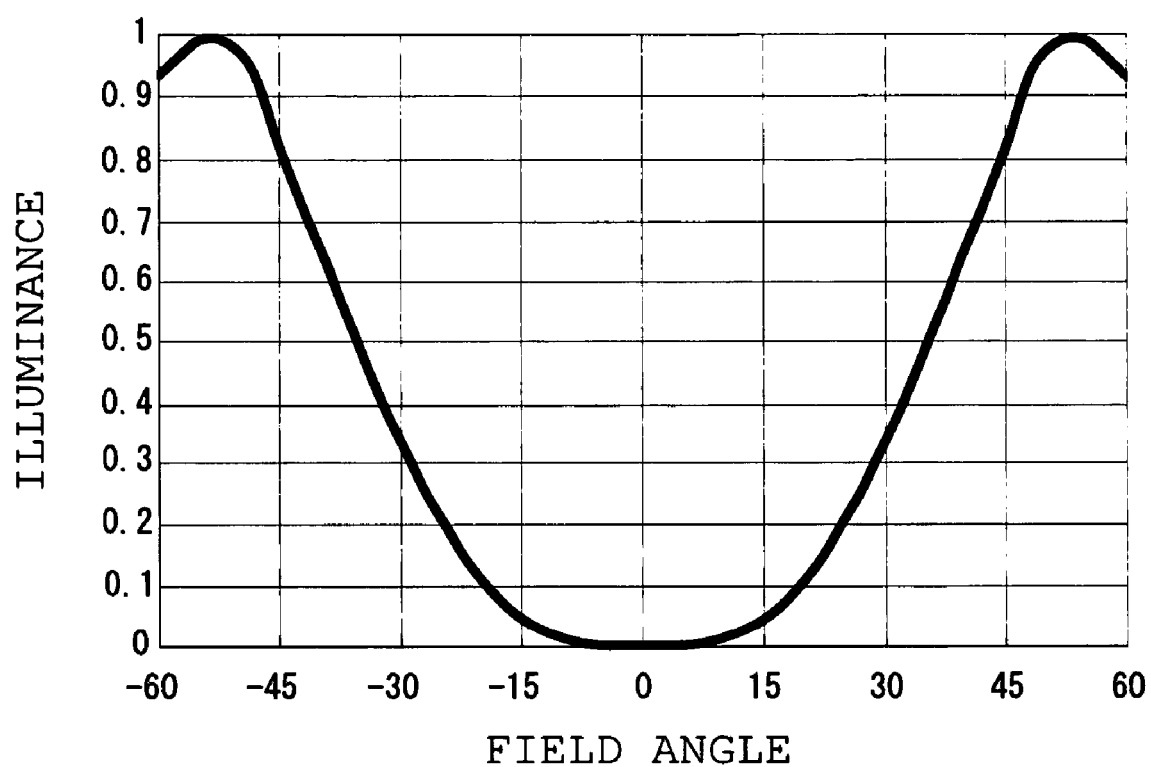
FIG. 10 is a graph showing the illuminance characteristic on the imaging surface of the image sensor when the objective optical system of FIG. 8A is used in the capsule type endoscope to image the inner wall of the white cylinder.

FIG. 8A shows the arrangement, developed along the optical axis, of an objective optical system used in a conventional endoscope. FIG. 8B shows the aberration characteristic of distortion in the objective optical system. FIG. 9 shows the illuminance characteristic of the objective optical system of FIG. 8A when the uniform surface illuminant is observed. FIG. 10 shows the illuminance characteristic of the imaging surface of the image sensor when the objective optical system of FIG. 8A is used in the capsule type endoscope to image the inner wall of the white cylinder.

In a capsule type endoscope 43 of the first embodiment, as show in FIG. 1A, a transparent cover 3 made from resin-based transparent material through pressure molding is provided at the most object-side position. Inside the transparent cover 3, an objective optical system 1 is placed in a state where it is fixed to a lens frame 37 for the objective optical system. The objective optical system 1, as shown in FIG. 1B, is surrounded with four chip LEDs 2 constituting the illumination means through the lens frame 37. At the position of the image plane of the objective optical system 1, as shown in FIG. 1A, a CMOS chip 38 constructed as the image sensor is located, and in order from behind the chip, an electric substrate 40, two button batteries 39 for supplying the CMOS and the LEDs with electricity, and an antenna unit 41 for transmitting a captured image to an image display system 25 placed outside the living body, illustrated in FIG. 2. The outer wall of the capsule type endoscope 43 is hermetically sealed by the transparent cover 3 and an outer cover 42.

The image display system 25, as illustrated in FIG. 2, is designed to have a personal computer 24 that is capable of processing the image signal and a monitor 23 displaying the image.

Also, as the image sensor, a CCD chip may be used instead of the CMOS chip 38.

The chip LEDs 2 constituting the illumination means are not limited to four in number and may have any of numbers of two, six, and eight, for instance.

The image signal transmitted by radio from the antenna unit 41 of FIG. 1A, as shown in FIG. 2, is received by an antenna unit 22 provided outside the body of a patient and after being processed by the personal computer 24, is displayed as an image on the monitor 23.

The objective optical system, as shown in FIG. 4A, includes, in order from the object side, a plane-parallel plate $1_1$, a plano-convex lens $1_2$ whose object-side surface is flat and whose image-side surface is convex, a plano-convex lens $1_3$ whose object-side surface is flat and whose image-side surface is convex, and a plano-convex lens $1_4$ whose object-side surface is convex and whose image-side surface is flat. The convex surface of the plano-convex lens $1_3$ is configured as an aspherical surface. An aperture stop S is interposed between the plane-parallel plate $1_1$ and the plano-convex lens $1_2$.

Subsequently, numerical data of the objective optical system constituting the capsule type endoscope of the first embodiment are shown below.

In the numerical data, f denotes a focal length; F, an F-number; IH, the image height of the image sensor; OBJ, an object distance; and ω, an angle of view at the maximum image height in the objective optical system.

Also, when Z is taken as the coordinate in the direction of the optical axis, y is taken as the coordinate normal to the optical axis, and the direction of travel of light is positive, an aspherical configuration Z (y) is expressed by the following equation:

$$Z(y) = \frac{(1/R) \cdot y^2}{1 + \sqrt{\{1 - (k+1) \cdot (1/R)^2 \cdot y^2\}}} + A2 \cdot y^2 + A4 \cdot y^4 + \ldots + An \cdot y^n$$

where R is the radius of curvature of the lens, k is a conic constant, A2 is the second order aspherical coefficient, A4 is the fourth order aspherical coefficient, and An is the nth order aspherical coefficient. It is necessary that the lens configuration, which is symmetrical about the optical axis, is constructed by the orders of even numbers.

These symbols are also used in the embodiments to be described later.

Numerical Data 1

| f = 1.000, F = 2.706, IH = 1.179, OBJ = 15.000, 2ω = 119.96 | | | | | |
|---|---|---|---|---|---|
| Face number | Radius of curvature | Face-to-face spacing | Refractive index | Abbe's number | k |
| 0 | INF | 15.0000 | 1 | | |
| 1 | INF | 0.5797 | 1.51633 | 64.50 | |
| 2 (Stop) | INF | 0.9697 | 1.72916 | 54.68 | |
| 3 | −1.4844 | 0.1932 | 1 | | |
| 4 | INF | 1.0771 | 1.56348 | 60.69 | |
| 5 (Aspherical) | −0.7176 | 0.1932 | 1 | | −1.8791 |
| 6 | 3.1282 | 0.6803 | 1.51633 | 64.15 | |
| 7 | INF | 0 | 1 | | |
| 8 (Imaging surface) | | | | | |

The fifth surface is an aspherical surface configured by the aspherical equation of the conic constant only. Also, INF means that the curvature is infinite (the surface is flat).

Illumination light with the light intensity distribution of FIG. 3, which is reflected by a side surface 50 of the cylindrical structure of the white cylinder shown in FIG. 7, passes through the objective optical system 1 of the first embodiment and is imaged on the imaging surface of the image sensor 38. In this case, when the inner wall of the cylinder is designed to have a reflectance of 90% relative to white light, the inside diameter D of the cylinder, the inside diameter D of the cylinder against the capsule with an outside diameter of 13 mm is 15.6 mm.

Also, in the capsule type endoscope of the first embodiment, an aspherical lens is used in the objective optical system, and as shown in FIG. 4B, the amount of production of distortion at the maximum image height is kept to 35% or less, thereby controlling the amount of light on the periphery of the visual field.

When the center axis of the white cylinder is made to coincide with the longitudinal center axis of the capsule, reflected light from the inner wall of the cylinder illuminated by the illumination means 2 of the capsule type endoscope, imaged on the imaging surface of the image sensor 38 through the objective optical system 1, possesses the illuminance distribution characteristic such as that shown in FIG. 6. Application of this to Conditions (1) and (2) gives $\omega=60°$ $T_1: T_2=1:0.65$ It is seen from this that the capsule type endoscope of the first embodiment satisfies Conditions (1) and (2). According to the capsule type endoscope of the first embodiment that satisfies conditions (1) and (2), a wide field region is provided, and when the cylindrical structure is observed, a favorable brightness distribution is obtained on the imaging surface of the image sensor 38 and it is avoidable to produce halation on the periphery of the visual field.

The signal of the image formed on the imaging surface of the image sensor 38, as mentioned above, is transmitted through the antenna unit 41, is received by an antenna unit 22, and after being processed by the personal computer 24, is displayed as an image on the monitor 23.

Also, the signal transmitted by the personal computer 24 from the antenna unit 41 is processed, for example, by γ correction, but in the first embodiment, correction is merely made by a reverse γ characteristic and brightness is not particularly adjusted. Consequently, the signal intensity distribution of the image displayed on the monitor 23 and the illuminance distribution of the imaging surface of the image sensor 38 have the same distribution profile. Thus, the intensity of the image signal output to the monitor is measured from the center of the image to the periphery to depict the intensity distribution of the image signal, and thereby the illuminance distribution of the imaging surface can be easily confirmed.

On the other hand, in a comparative example where the size of the capsule type endoscope and the illumination optical system are the same as in the above condition and only the objective optical system is used as the conventional objective optical system shown in FIG. 8A, its aberration characteristic, as illustrated in FIG. 8B, has strong distortion at the maximum image height identical with the case of FIG. 4B. As a result, in the illuminance characteristic on the imaging surface of the image sensor 38 where the inner wall of the white cylinder is observed, as shown in FIG. 9, the periphery is so bright that halation is liable to occur on the periphery of the visual field and a favorable observation image cannot be obtained.

Application to Conditions (1) and (2) gives $\omega=60°$ $T_1:T_2=1:0.32$

It is thus seen that the capsule type endoscope fails to satisfy Condition (2). In the capsule type endoscope of a comparative example that fails to satisfy Condition (2), besides the fact that halation is liable to occur on the periphery of the visual field, the center portion of the image becomes dark, and when the cylindrical structure is observed, a favorable brightness distribution is not obtained.

Second Embodiment

Figure 11:
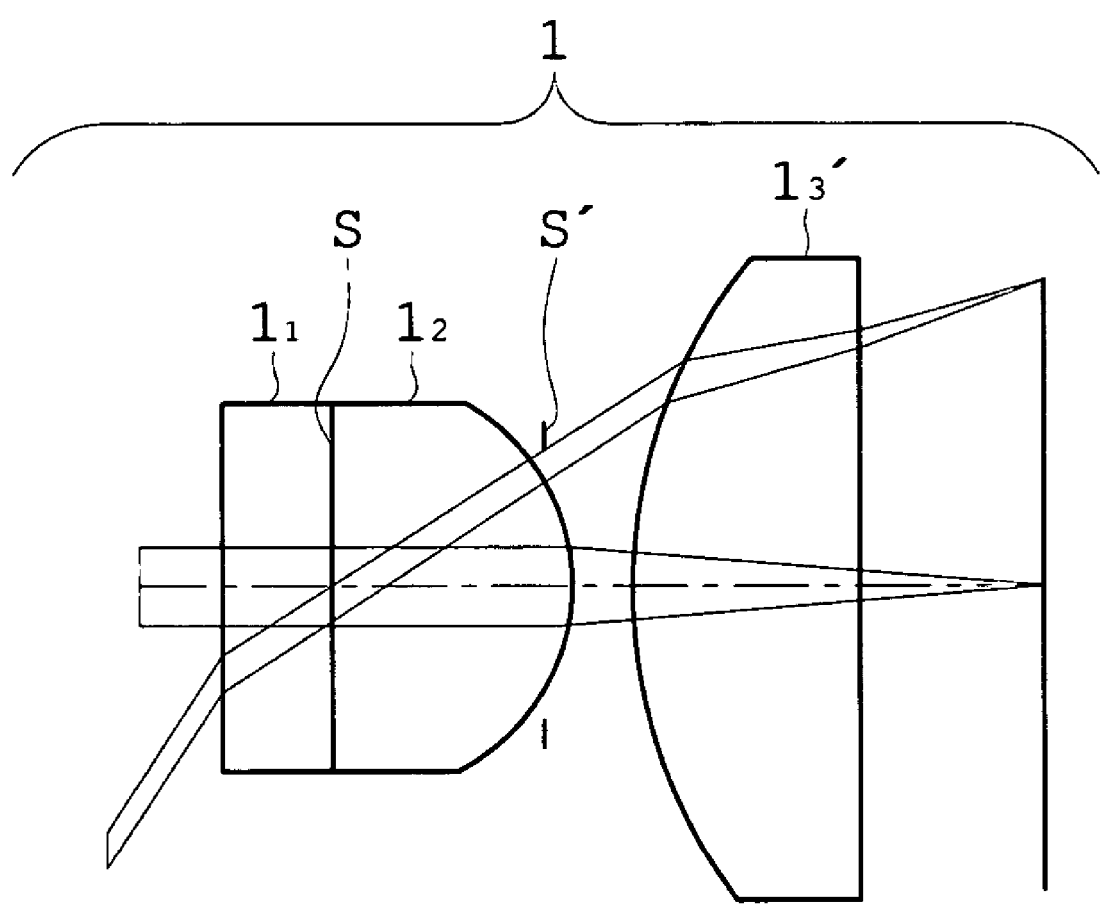
FIG. 11 is a sectional view showing the arrangement, developed along the optical axis, of the objective optical system in the capsule type endoscope of a second embodiment of the present invention.
Figure 12:
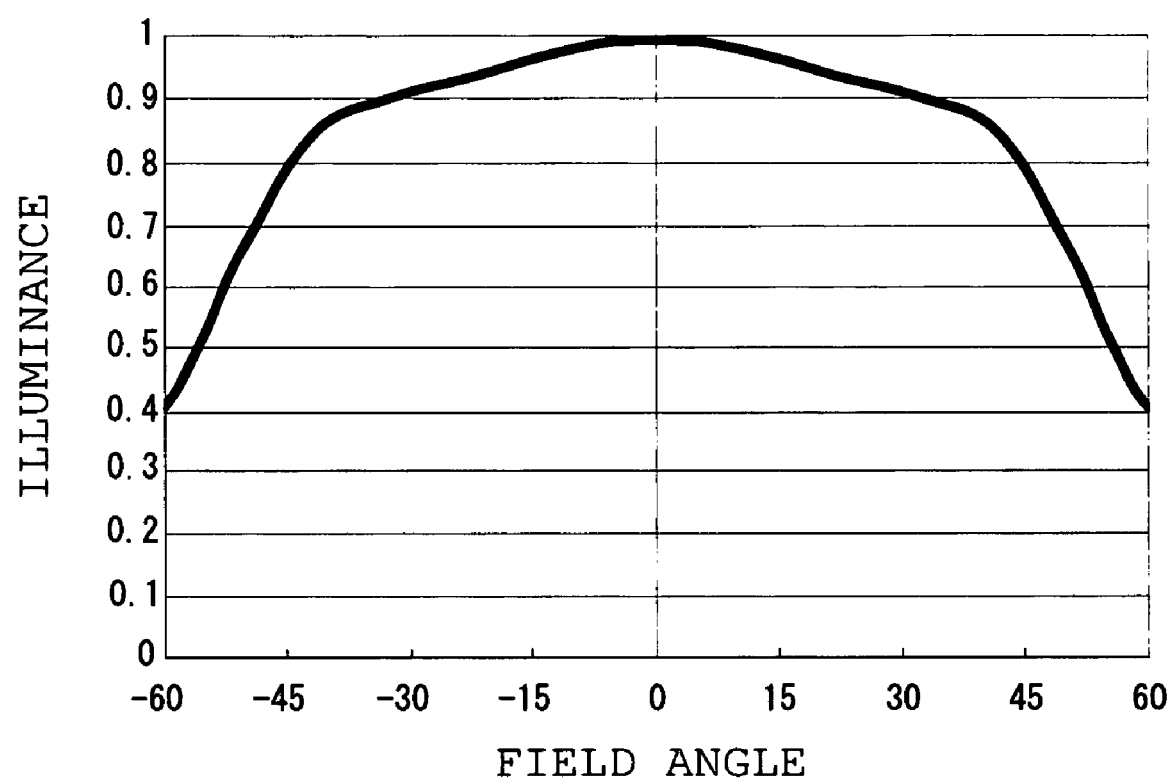
FIG. 12 is a graph showing the characteristic of illuminance plotted against the field angle of the objective optical system when the uniform surface illuminant is observed.
Figure 13:
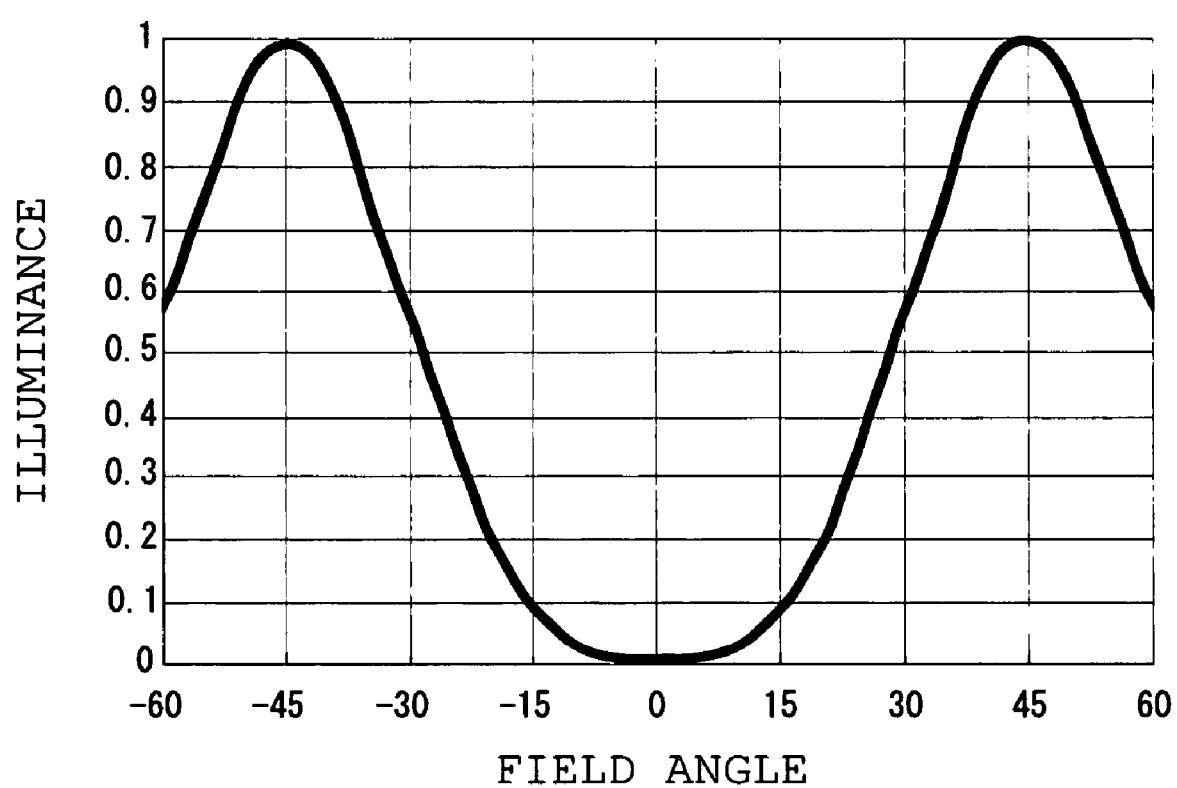
FIG. 13 is a graph showing the characteristic of illuminance of the imaging surface of the image sensor plotted against the field angle of the objective optical system when the inner wall of the white cylinder is imaged in the capsule type endoscope of the second embodiment.

FIG. 11 shows the arrangement, developed along the optical axis, of the objective optical system in the capsule type endoscope of the second embodiment of the present invention. FIG. 12 is a graph showing the characteristic of illuminance plotted against the field angle of the objective optical system when the uniform surface illuminant is observed. FIG. 13 is a graph showing the characteristic of illuminance of the imaging surface of the image sensor plotted against the field angle of the objective optical system when the inner wall of the white cylinder is imaged in the capsule type endoscope of the second embodiment.

In the second embodiment, the size of the capsule type endoscope and the illumination optical system are the same as in the first embodiment. Only the objective optical system, which uses the arrangement shown in FIG. 11, is different from that of the first embodiment.

The objective optical system 1 includes, in order from the object side, the plane-parallel plate 1$_1$, the plano-convex lens 1$_2$ whose object-side surface is flat and whose image-side surface is convex, and a plano-convex lens 1$_3$' whose object-side surface is convex and whose image-side surface is flat. The aperture stop S is interposed between the plane-parallel plate 1$_1$ and the plano-convex lens 1$_2$. A flare stop is also interposed between the plano-convex lens 1$_2$ and the plano-convex lens 1$_3$'.

Subsequently, numerical data of the objective optical system constituting the capsule type endoscope of the second embodiment as shown below.

Numerical Data 2

| f = 1.2331, F = 4.473, IH = 1.179, OBJ = 11.9731, 2ω = 119.96 | | | | | |
|---|---|---|---|---|---|
| Face number | Radius of curvature | Face-to-face spacing | Refractive index | Abbe's number | k |
| 0 | INF | 11.9731 | 1 | | |
| 1 | INF | 0.3862 | 1.51633 | 64.15 | |
| 2 (Stop) | INF | 0.8690 | 1.51633 | 64.15 | |
| 3 | −0.8536 | −0.0984 | 1 | | |
| 4 (F stop) | INF | 0.3107 | 1 | | 1.08 |
| 5 | 2.1841 | 0.8111 | 1.51633 | 64.15 | |
| 6 | INF | 0.6571 | 1 | | |
| 7 (Imaging surface) | | | | | |

Illumination light with the light intensity distribution of FIG. 12, which is reflected by the inner surface 50 of the white cylinder shown in FIG. 7, passes through the objective optical system 1 of the second embodiment and is imaged on the imaging surface of the image sensor 38. At this time, in the objective optical system 1 of the second embodiment, as shown in FIG. 11, marginal light is blocked through the flare stop S' interposed as a light-blocking member between the first convex lens 1$_2$ and the second convex lens 1$_3$', and the brightness distribution of the imaging surface of the image sensor 38 is controlled.

Reflected light imaged on the imaging surface of the image sensor 38 possesses the illuminance characteristic such as that shown in FIG. 12. Application of this to Conditions (1) and (2) gives $$\omega = 60°$$

$$T_1 : T_2 = 1 : 0.54$$

From this, it is seen that the capsule type endoscope of the second embodiment satisfies Conditions (1) and (2). According to the capsule type endoscope of the second embodiment that satisfies Conditions (1) and (2), a wide field region is provided, and when the cylindrical structure is observed, halation can be prevented from occurring on the periphery of the visual field and the brightness distribution suitable for the observation of the inner wall of the cylinder relative to the imaging surface of the image sensor 38 is obtained.

For the placement of the light-blocking member blocking marginal rays, when it is located in the proximity of the image plane, the proportion of blocking of a light beam on the periphery of the visual field is changed according to fabrication and assembly errors of the light-blocking member, and there is the possibility that the phenomenon, called "vegnetting", which becomes rapidly dark on the periphery of the image is prominent. It is thus desirable that the light-blocking member is located in proximity of the exit pupil.

Also, in the second embodiment, the flare stop is used as the light-blocking means, but even in the use of the light-blocking means for marginal light applying the mechanical frame of a space tube or chamfering and black ink on the lens periphery, the same effect is brought about. Even when an ND filter designed to attenuate the intensity of the light beam on the periphery of the visual field is placed, the same effect is secured.

In the objective optical system 1 of the second embodiment, although each of the first convex lens 1₂ and the second convex lens 1₃' is configured as an aspherical lens, either the first convex lens 1₂ or the second convex lens 1₃' may be configured as the aspherical lens.

In the lens arrangement, two convex lenses are used, but a single aspherical lens may be used.

Third Embodiment

Figure 14:
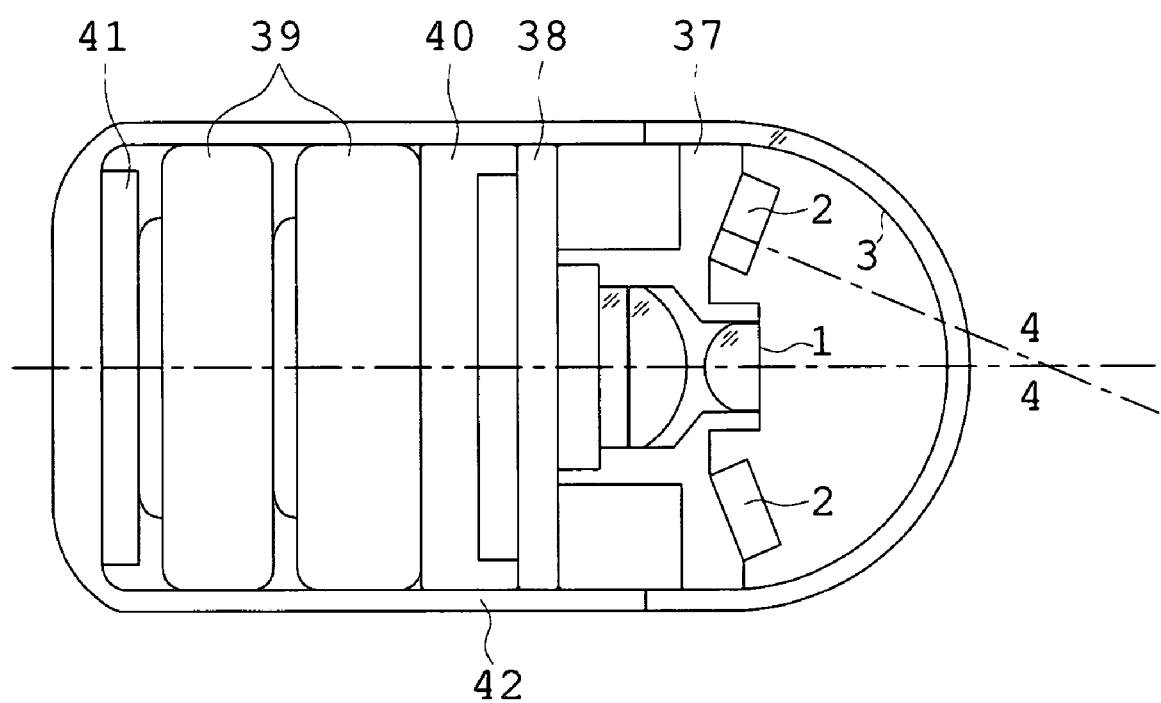
FIG. 14 is a sectional view showing schematically the structure, exhibited along the optical axis, of the capsule type endoscope of a third embodiment in the present invention.
Figure 15:
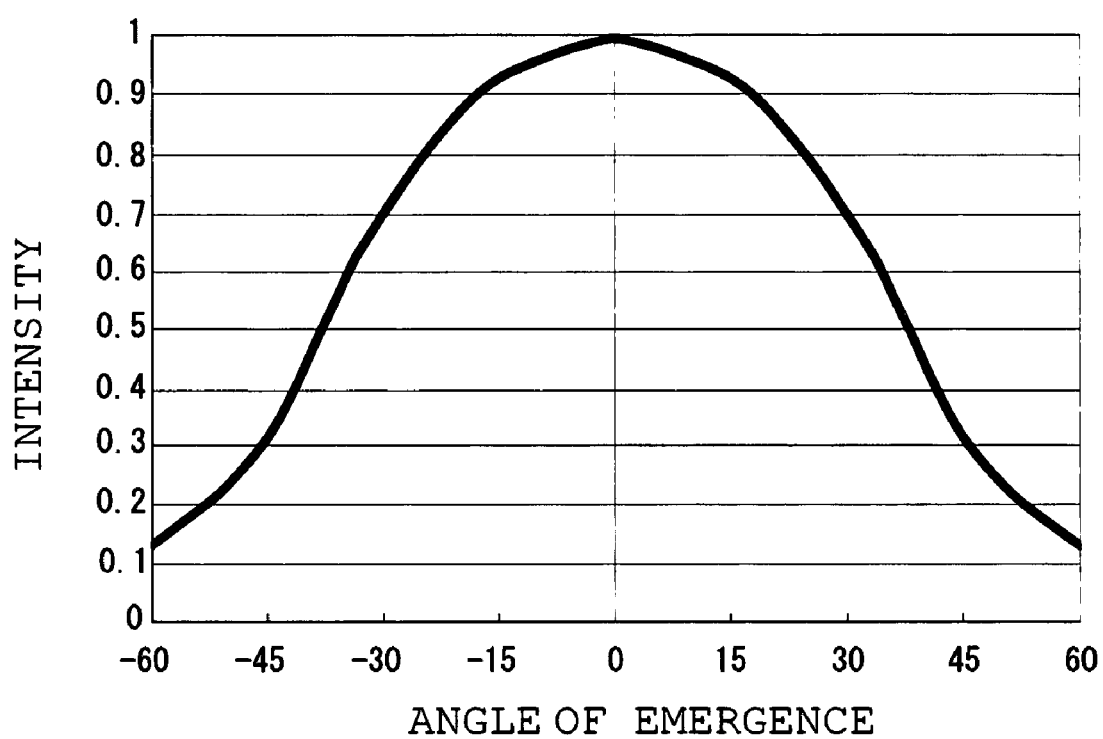
FIG. 15 is a graph showing the distribution of the intensity of illumination light plotted against the angle of emergence of light of the illumination means in the capsule type endoscope of the third embodiment.
Figure 16:
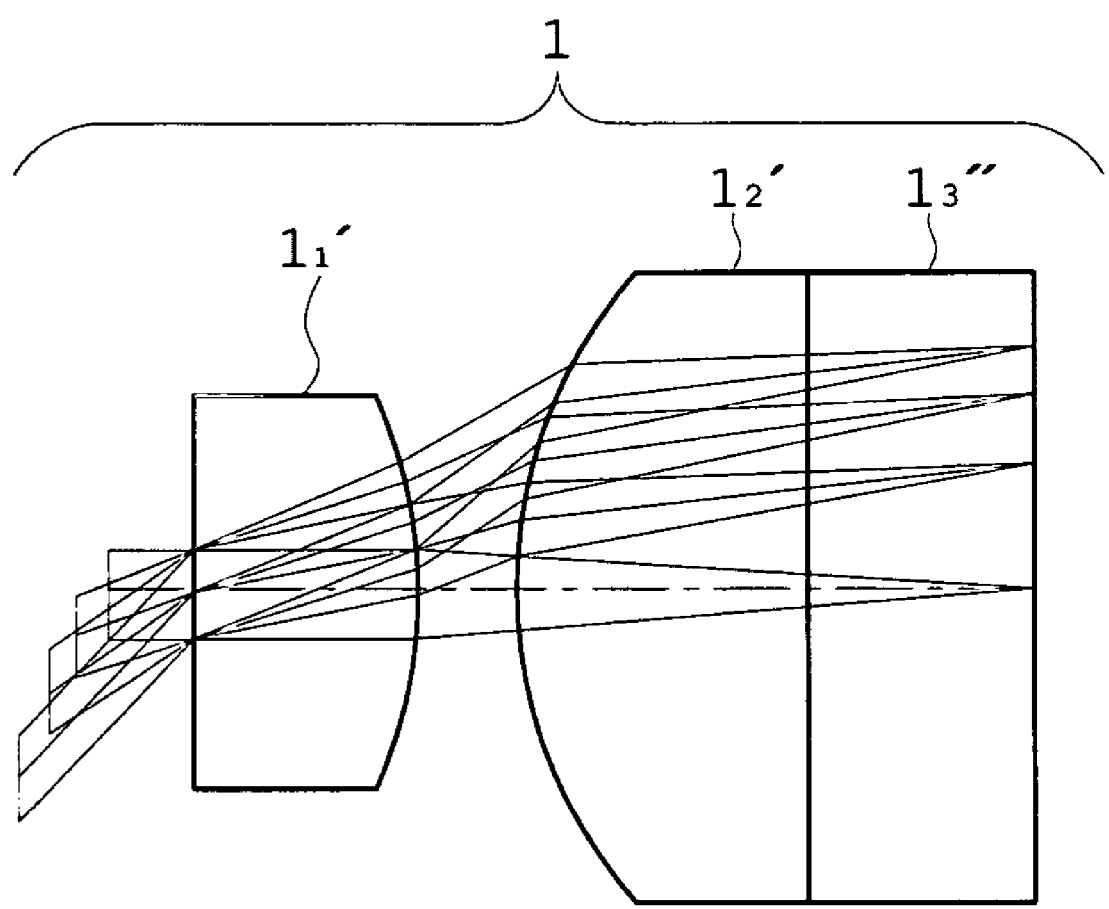
FIG. 16 is a sectional view showing the arrangement, developed along the optical axis, of the objective optical system in the capsule type endoscope of the third embodiment.
Figure 17:
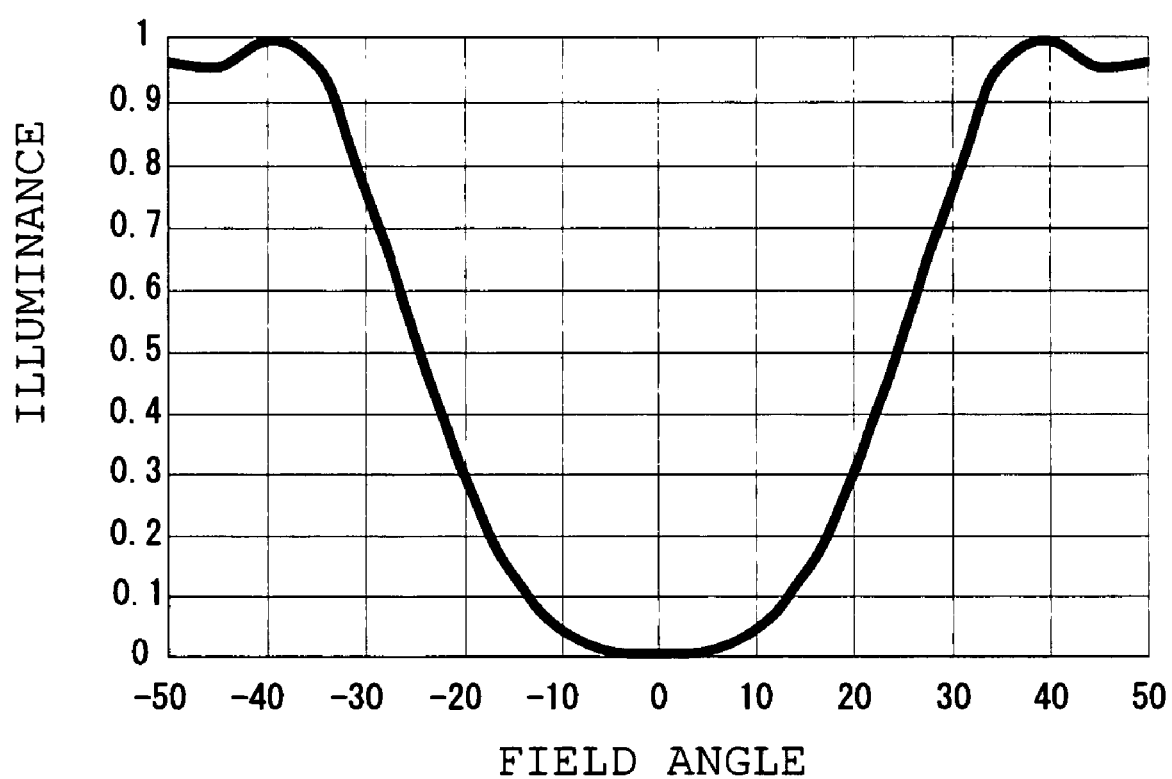
FIG. 17 is a graph showing the distribution characteristic of illuminance of the imaging surface of the image sensor plotted against the field angle of the objective optical system when the inner wall of the white cylinder is imaged in the capsule type endoscope of the third embodiment.

FIG. 14 shows the structure, exhibited along the optical axis, of the capsule type endoscope of the third embodiment in the present invention. FIG. 15 is a graph showing the distribution of the intensity of illumination light plotted against the angle of emergence of light of the illumination means in the capsule type endoscope of the third embodiment. FIG. 16 shows the arrangement, developed along the optical axis, of the objective optical system in the capsule type endoscope of the third embodiment. FIG. 17 is a graph showing the distribution characteristic of illuminance of the imaging surface of the image sensor plotted against the field angle of the objective optical system when the inner wall of the white cylinder is imaged in the capsule type endoscope of the third embodiment.

The capsule type endoscope of the third embodiment, as shown in FIG. 14, is such that the center axis of the illumination means 2 provided in the capsule type endoscope is inclined at some angle with respect to the optical axis of the objective optical system 1.

As mentioned above, the center axis of the illumination means 2 is inclined with respect to the optical axis of the objective optical system, and thereby when a spherical object located, for example, about 50 mm in front of the objective optical system is illuminated, it becomes possible to adjust the illuminance distribution of the object surface so as to satisfy Condition (4). Whereby, when such a spherical object is imaged, it is possible to correct a phenomenon attributable to the aberration characteristic of the objective optical system of a wide field angle that the illuminance of the imaging surface of the image sensor increases progressively in going from the center of the visual field to the periphery, and thus it is also possible to control the illuminance distribution characteristic of the surface of the image sensor where the inner wall of the cylinder is imaged. The illuminance distribution of the imaging surface of the image sensor against the field angle of the objective optical system, controlled by considering the illumination means as mentioned above, is capable of assuming the distribution profile equivalent to the illuminance distribution of each of Types B and C in FIG. 18, obtained when the objective optical system is considered.

Also, the considerations of the illumination means and the objective optical system, described above, may be together taken.

The objective optical system 1 of the third embodiment includes, in order from the object side, a plano-convex lens 1₁', whose object-side surface is flat and whose image-side surface is convex, a plano-convex lens 1₂' whose object-side surface is convex and whose image-side surface is flat, and a plane-parallel plate 1₃".

Subsequently, numerical data of the objective optical system constituting the capsule type endoscope of the third embodiment as shown below.

Numerical Data 3

| f = 1.558, F = 3.829, IH = 1.179, OBJ = 14.339, 2ω = 100.19 | | | |
|---|---|---|---|
| Face number | Radius of curvature | Face-to-face spacing | Refractive index | Abbe's number |
| 0 | INF | 14.3390 | 1 | |
| 1 | INF | 1.0156 | 1.88300 | 40.76 |
| 2 | −2.3916 | 0.4570 | 1 | |
| 3 | 2.6938 | 1.2694 | 1.88300 | 40.76 |
| 4 | INF | 1.0156 | 1.61090 | 50.20 |
| 5 (Imaging surface) | | | | |

Figure 19:
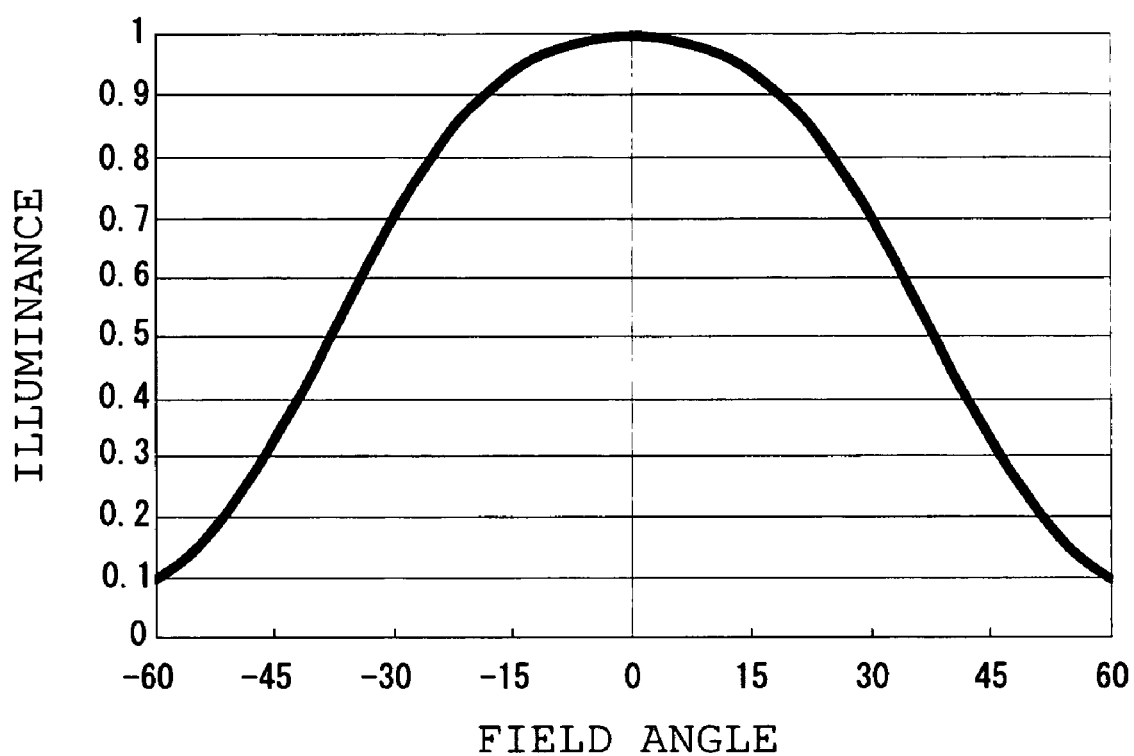
FIG. 19 is a diagram showing the illuminance distribution of the surface of the spherical object located 50 mm in front of the most object-side surface of the objective optical system in the capsule type endoscope of the third embodiment.

Illumination light with the light intensity distribution of FIG. 15, which is reflected by the inner surface 50 of the white cylinder shown in FIG. 7, passes through the objective optical system 1 of the third embodiment and is imaged on the imaging surface of the image sensor 38. In this case, the center axis of the illumination means 2 is inclined at an angle of nearly 25° C. with the optical axis of the objective optical system 1, and the illuminance distribution of the surface of the spherical object located 50 mm in front of the most object-side surface of the objective optical system 1 practically assumes the profile shown in FIG. 19. From this, it is seen that Condition (4) is satisfied.

Reflected light imaged on the imaging surface of the image sensor 38 possesses the illuminance characteristic such as that shown in FIG. 17. Application of this to Conditions (1) and (2) gives $$\omega = 50.1°$$

$$T_1 : T_2 = 1 : 0.51$$

From this, it is seen that the capsule type endoscope of the third embodiment satisfies Conditions (1), (2), and (4).

According to the capsule type endoscope of the third embodiment, a wide field region is provided, and when the cylindrical structure is observed, halation can be prevented from occurring on the periphery of the visual field and the brightness distribution suitable for the observation of the inner wall of the cylinder relative to the imaging surface of the image sensor 38 is obtained.

Also, in the capsule type endoscope of the third embodiment, the illumination means is considered so that the center axis of the illumination means is inclined with respect to the optical axis of the objective optical system. However, even when an optical element controlling the distribution of light is located immediately behind the illumination means so that the distribution of illumination light is controlled, the same effect is brought about.

The capsule type endoscope may be designed so that a light-blocking member or a member attenuating the intensity of illumination light is located immediately behind the illumination means and part of illumination light emitted form the illumination means is blocked or attenuated, thereby controlling the distribution of illumination light.

The capsule type endoscope may also be designed so that a plurality of LEDs, each having a narrow-angle light distribution, are used as a light source and an angle made by the objective optical system with the center axis of each LED is adjusted, thereby controlling the distribution of illumination light.

The components of the capsule type endoscopes of the above embodiments may be partially combined. It is needless to say that such a combined capsule type endoscope comes into the category of the capsule type endoscope of the present invention.

Fourth Embodiment

Figure 21:
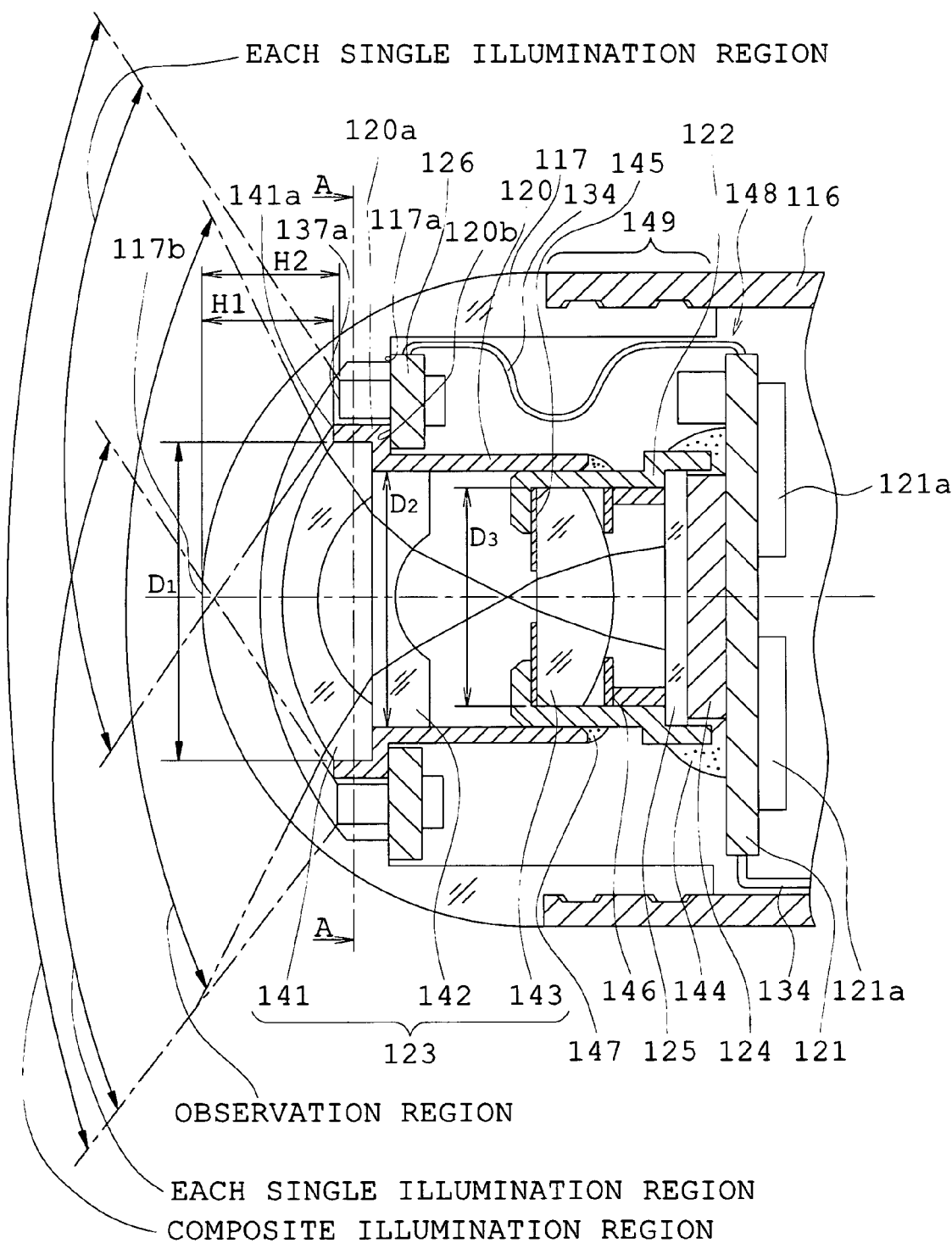
FIG. 21 is an enlarged view showing the distal end of the capsule type endoscope of a fourth embodiment in the present invention.

This embodiment, as shown in FIG. 21, is constructed so that the lens configuration of an objective optical system 123 is considered to carry out observations in a field region as wide as at least 140° C.

In accordance with FIG. 21, the structure of the distal end of a capsule type endoscope 103 will be described in detail below. In the capsule type endoscope 103, as shown in the figure, a second lens frame 122 is fitted into the rear end side of a first lens frame 120. The objective optical system 123 includes, in order form the object side, a first lens 141, a second lens 142, and a third lens 143.

In the first lens frame 120, the first lens 141 is supported by and fixed to an enlarged portion 120*a* of the inside diameter of the frame, while behind the first lens 141, the second lens 142 is supported by and fixed to a reduced portion smaller in the inside diameter of the frame than the enlarged portion 120*a*. On the other hand, an aperture stop 145, the third lens 143, and a flare-proof stop 146, arranged in this order from the object side, are supported by and fixed to the second lens frame 122, and behind these, a cover glass 125 of an image sensor is fitted into the second lens frame 122 and is cemented and fixed to an imaging substrate 121 by a light-blocking adhesive 144.

The second lens frame 122 is fitted into the rear end side of the first lens frame 120 and is cemented to and fixed to first lens frame 120 by an adhesive 147 after the first lens frame 120 and the second lens frame 122 are relatively moved for focus adjustment. In this way, an imaging section 148 is constructed. In addition, on the peripheral side of the first lens frame 120, an illumination substrate 126 is placed to abut a surface 120*b* perpendicular to the enlarged portion 120*a*.

A transparent cover 117 is fitted into a sheath section 116 of the capsule and is cemented and fixed thereto in a watertight fashion by a watertight adhesive. The fitting portion that the transparent cover 117 is fitted into the sheath section 116 of the capsule is provided with a snap section 149 configured to mutually have concavities and convexities, and the watertight adhesive is applied to clearance between them. Also, the transparent cover 117 is provided with an abutting surface 117 so that the illumination substrate 126 abuts it.

Here, in the fourth embodiment, the first lens 141 is configured to be larger than the outside diameter of each lens located behind the first lens 141 and to have a convex surface facing the object side. An outside diameter D1 of the first lens 141 is such as to satisfy the relation, $D1>D2 \geq D3$, with respect to an outside diameter D2 of the second lens 142 and the outside diameter D3 of the third lens 143. The first lens 141 is configured into a meniscus shape with a convex surface facing the object side and has negative refracting power. Whereby, the first lens 141, in contrast with the conventional lens, is capable of capture light from a wide range so that this light can be imaged on the imaging surface of a CMOS imager 124 through the second lens 142 and the third lens 143.

The second lens 142 is configured into a plano-concave shape and is placed so that a light beam on the periphery of the visual field is not eclipsed and is incident on the aperture stop 145.

In the fourth embodiment, an arrangement is made such that a top surface 137*a* of each of illumination sections 137 is made to nearly coincide with, or is located behind, a top surface 141*a* of the first lens frame 120. More specifically, the top surface 137*a* of the illumination section 137 is located so that a distance H2 from a top surface 117*b* of the transparent cover 117 to the top surface 137*a* of the illumination section 137 and a distance H1 from the top surface 117*a* of the transparent cover 117 to the top surface 141*a* of the first lens frame 120 satisfy the relation, $H2 \geq H1$.

Figure 22:
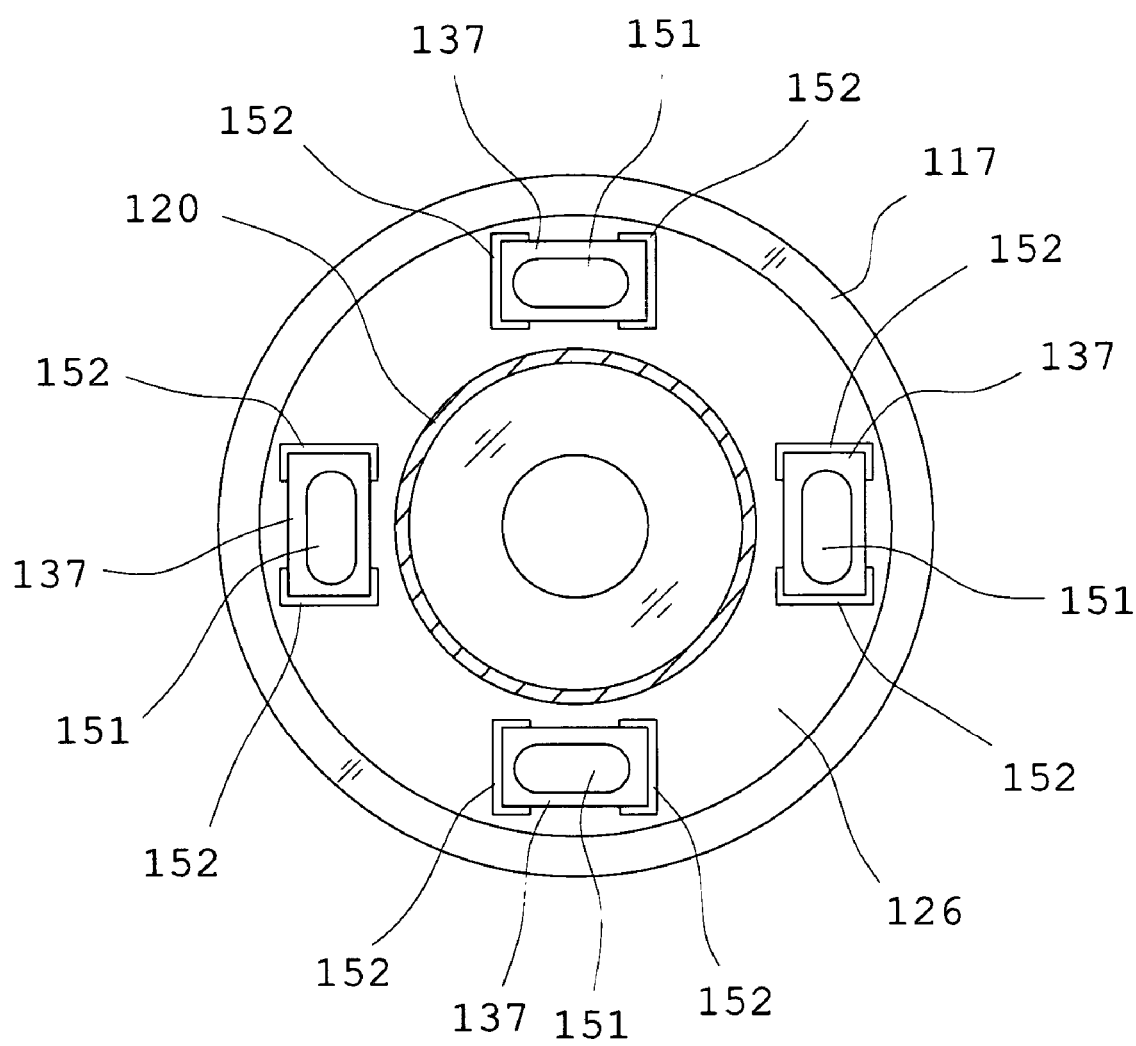
FIG. 22 is a sectional view showing the arrangement of illumination sections of the fourth embodiment.

FIG. 22 shows the arrangement of the illumination sections 137. The illumination sections 137 are arranged symmetrically about the longitudinal center axis of the capsule in such a way that they surround the first lens frame 120. White LEDs 151 are adopted as light-emitting elements. Also, in FIG. 22, reference numeral 152 designates connecting electrodes provided on the illumination substrate 126, which are electrically connected to the illumination sections 137.

Figure 23:
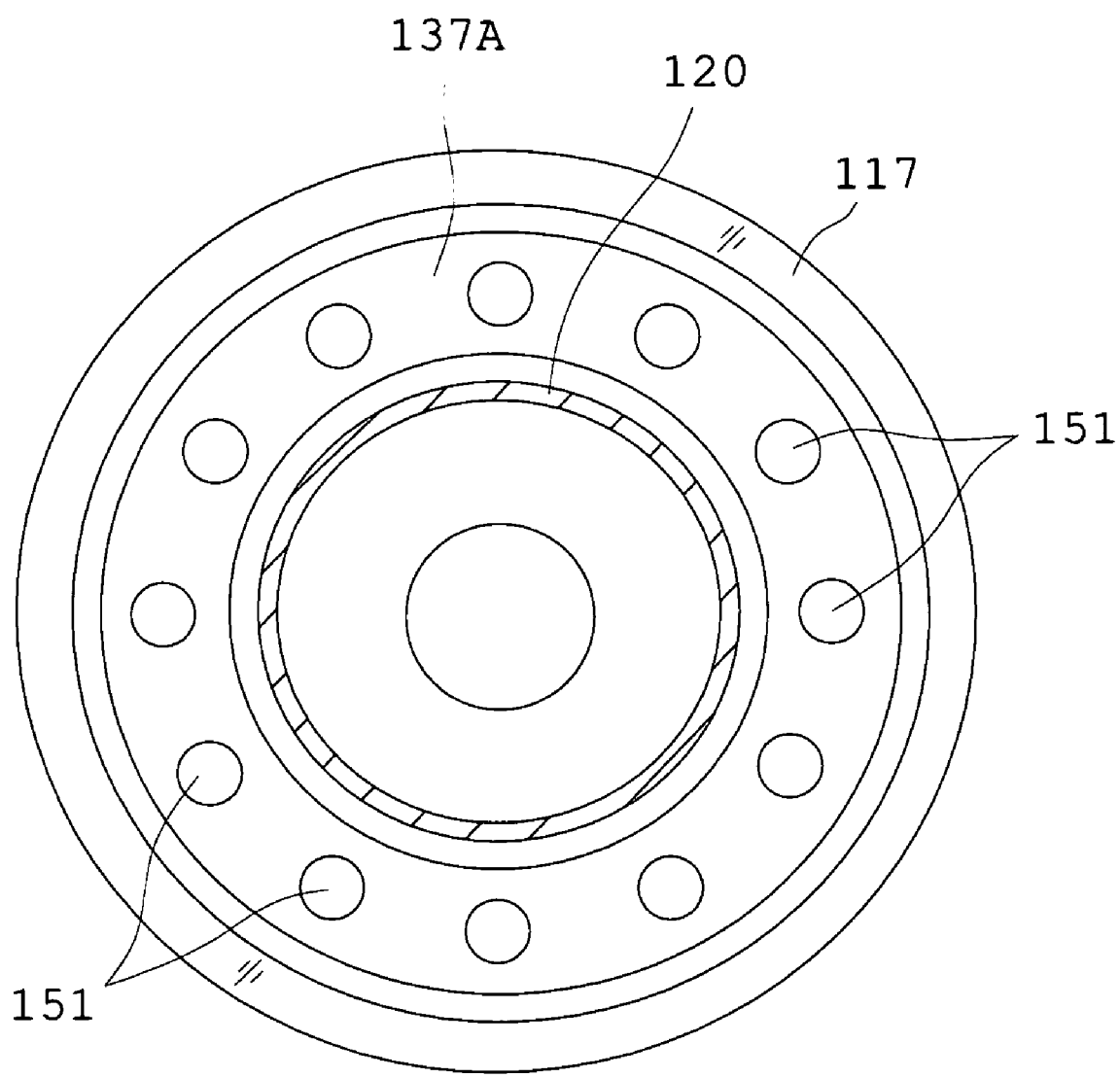
FIG. 23 is a sectional view showing a modified example of the arrangement of the illumination sections of the fourth embodiment.

FIG. 23 shows a modified example of the arrangement of the illumination sections. In this example, an illumination section is annularly configured. In an annular illumination section 137A of FIG. 23, the white LEDs 151 are arranged concentrically with respect to the longitudinal center axis of the capsule. In this case, the annular illumination section 137A, because of its narrow space, can be provided with many white LEDs 151, and thus even the periphery of the visual field can be illuminated with bright light. In the fourth embodiment, 12 white LEDs 151 are arranged. Single illumination regions of a plurality of white LEDs 151 overlap and thereby a composite illumination region is constructed. The observation region of the capsule type endoscope 103 is contained in the composite illumination region, and light reflected from an object located in the observation region that has a wide angle of 140° or more is captured by the first lens 141 of the objective optical system 123 and is imaged by the CMOS imager 124.

Some of the white LEDs 151 may be combined with one of band-pass filters shown in FIGS. 26A–26C to provide illumination for NBI. In this case, a cylindrical fixture with proper reflectance is provided in the inner wall and is fixed so that the center axis of the cylinder coincides with the longitudinal center axis of the capsule, and brightness is measured. Whereby, the numbers of LEDs emitting white light and narrow-band light for NBI can be set to reach the optimal proportion. For example, in the capsule type endoscope of the fourth embodiment whose outside diameter Φ is 13 mm, when the inner wall of the cylindrical fixture is designed to have a reflectance of 90% with respect to white light, the inside diameter D of the cylindrical fixture is calculated at 23 mm from Condition (8). Thus, in a state where the capsule type endoscope is fixed to the cylindrical fixture that has the inner wall surface in which the inside diameter is set to 23 mm and the reflectance relative to white light is designed to be 90%, the inner wall surface is illuminated by the LEDs emitting narrow-band light, provided in the capsule type endoscope, and the image of the inner wall surface is formed by the imaging means. Similarly, the inner wall surface is illuminated by the LEDs emitting white light, provided in the capsule type endoscope, and the image of the inner wall surface is formed by the imaging means. In this case, the intensities of the image signals output to the display device are measured in the range from the center of the image to the periphery and the maximum intensity values $S_c$ and $S_m$ of the image signals are extracted. The numbers of individual LEDs are adjusted so that Condition (10) is satisfied. Of 12 LEDs in the fourth embodiment, therefore, 4 LEDs emit white light and 8 LEDs emit narrow-band light for NBI.

Fifth Embodiment

Figure 24:
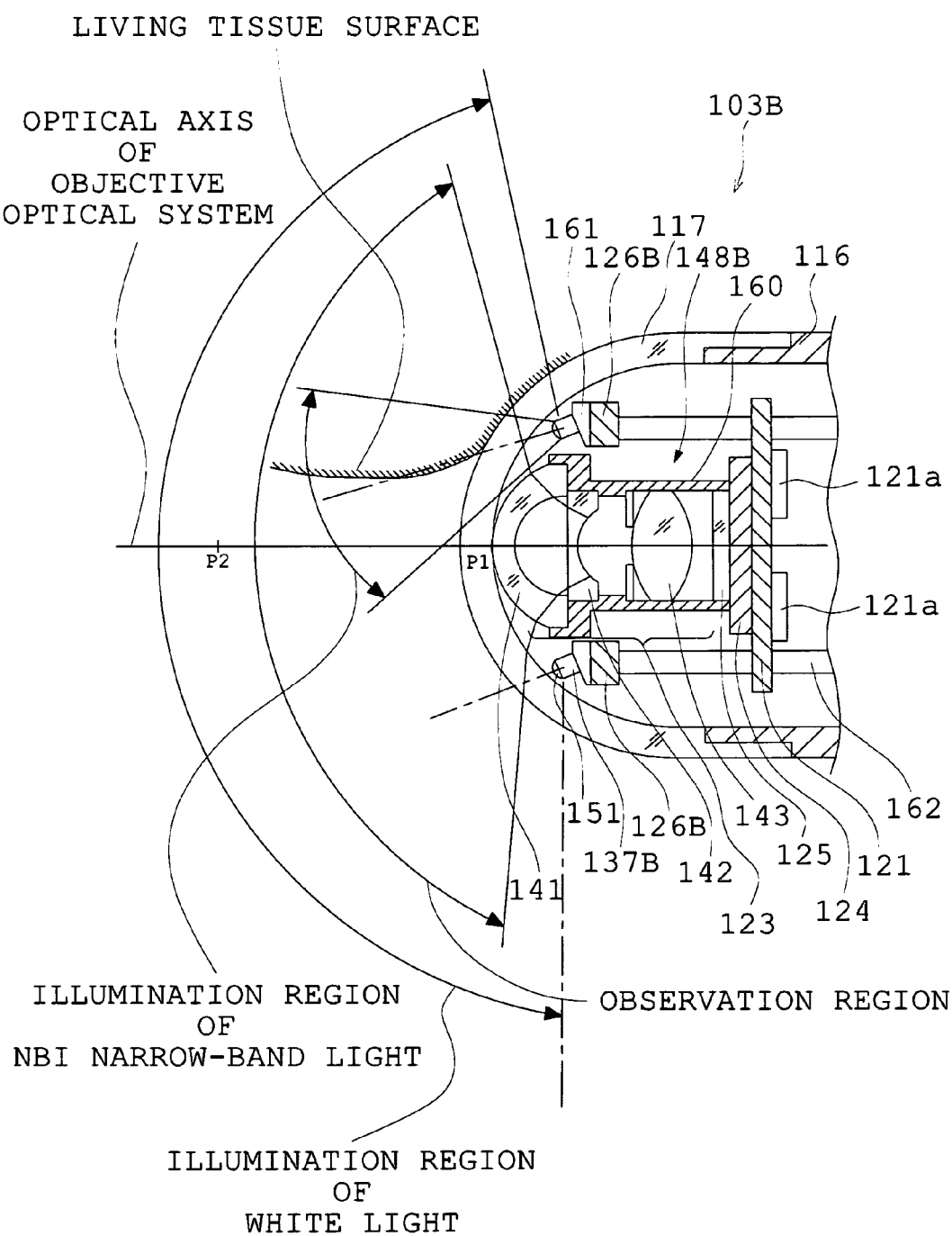
FIG. 24 is a sectional view showing the relationship between the observation field of the objective optical system and the illumination region of LEDs, enlarging the distal end of the capsule type endoscope of a fifth embodiment in the present invention.
Figure 25:
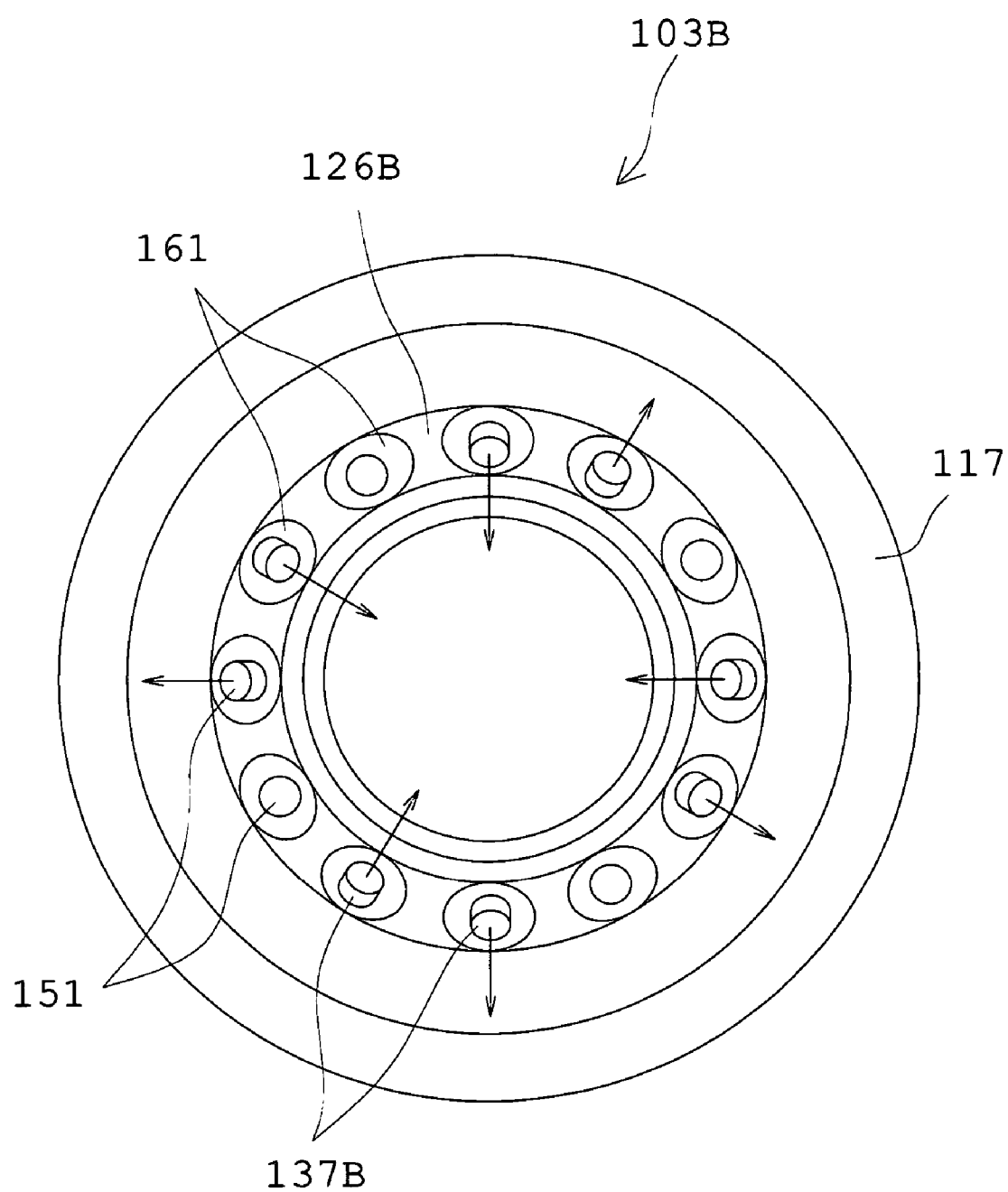
FIG. 25 is a view showing the arrangement of the illumination means of the capsule type endoscope, viewed from the object side, in the case where a transparent cover is removed in the fifth embodiment.

FIG. 24 shows the relationship between the observation field of the objective optical system and the illumination region of LEDs, enlarging the distal end of the capsule type endoscope of the fifth embodiment in the present invention. FIG. 25 shows the arrangement of the illumination means of the capsule type endoscope, viewed from the object side, in the case where a transparent cover is removed in the fifth embodiment.

In the fourth embodiment mentioned above, the first lens 141 of the objective optical system 123 is spaced away from the transparent cover 117, but the fifth embodiment is constructed so that the first lens 141 of the objective optical system 123 comes in close contact with the transparent cover 11. Since other features of the structure are the same as in the fourth embodiment, their explanation is omitted and like numerals are used for like members.

In the fifth embodiment, as in the fourth embodiment, the first lens 141 of the objective optical system 123 is configured to be larger than the outside diameter of each of the second and third lenses 142 and 143 located behind the first lens 141 and to have a convex surface facing the object side. These lenses and the cover glass 125 of the CMOS imager 124 are supported by and fixed to a lens frame 160, constituting an imaging section 148B. The first lens 141 of the objective optical system 123 approaches the transparent cover 117 and is brought into close contact therewith. Whereby, the overall length of the capsule is reduced and compactness is achieved. In the fifth embodiment, illumination sections 137B is different in arrangement. Each of the illumination sections 137B, as shown in FIG. 25, is provided with a tilting base 161 on the front side of an illumination substrate 126B configured into a doughnut shape so that the white LED 151 makes a preset angle with the optical axis of the objective optical system 123, not shown. Also, each illumination section 137B is connected to an LED driving circuit through a connecting terminal 162. By such a structure, it is possible to provide illumination with a desired light distribution characteristic relative to the observation field of the objective optical system 123. Like the fourth embodiment, some of the white LEDs 151 may be combined with one of band-pass filters shown in FIGS. 26A–26C to provide illumination for NBI. For example, a band-pass filter selectively transmitting light in a blue region, such as that shown in FIG. 26A, is used, and thereby it is possible to clearly depict the structure of capillary tubes distributed on the surface layer of the living tissue. Furthermore, by a combination with the imaging section in which a close-up image of the object is enlarged with a magnification of about 70–500× and can be displayed on the screen of a display device such as a monitor, it is possible to clearly depict the pit pattern of a lesion such as a tumor produced in the living tissue.

It is considered that the interior of the tubular organ, such as the small intestine, through which the capsule type endoscope travels, shrinks to obstruct the visual field of the capsule type endoscope. The capsule type endoscope travels in such a way as to push aside the inner wall of the tubular organ due to its vermicular motion. As shown in FIG. 24, therefore, the object-side surface of the transparent cover 117 tends to be in close contact with the inner wall of the tubular organ in the proximity of the peripheral boundary of the visual field. Thus, when the resolution of the imaging section 148B including the objective optical system 123 and the image sensor 124, such as the CMOS imager, is set so as to become highest in the proximity of the object-side surface of the transparent cover 117, the magnified image of the living tissue can be acquired. Specifically, in FIG. 24, it is desirable that the resolution at an object distance P1, taken along the optical axis, from the most object-side surface of the objective optical system 123 to the object-side surface of the transparent cover 117 coming in contact with the inner wall of the tubular organ is at least 5 lines/mm. At an object distance P2 in the proximity of the far point of the depth of field of the objective optical system 123, it is desirable that the resolution is at least 1 line/mm.

Here, the resolution of an ordinary imaging unit is defined as described below. Pairs of white and black lines placed in front of the objective optical system are imaged by the imaging unit in such a way that the white and black lines are arranged in a horizontal direction on the imaging surface of the solid-state image sensor, and are displayed on a monitor through a circuit system processing an image signal transmitted from the solid-state image sensor. In this case, when the maximum value and the minimum value of the intensity distribution of the white and black lines are denoted by Imax and Imin, a contrast I of the pairs of white and black lines on the monitor is found from $I=(Imax-Imin)/(Imax+Imin)$ The resolution is defined as the reciprocal of the width of the pairs of white and black lines where the contrast I is 10%.

Thus, "a resolution of at least 5 lines/mm" and "a resolution of at least l line/mm" described above indicate that the contrast of the pairs of white and black lines with widths of 0.2 mm or less and 0.5 mm or less, respectively, is 10% or less. When the resolution of the imaging unit is at least 5 lines/mm at the object distance P1, the living tissue located in the proximity of the object-side surface of the transparent cover can be magnified and observed on the screen of the monitor. When the resolution of the imaging unit is at least 1 line/mm at the object distance P2, the lesion, such as the tumor, produced on the inner wall surface of the tubular organ is easily found.

With respect to illumination light for NBI, it is desirable that the living tissue located in the proximity of the object-side surface of the transparent cover is efficiently illuminated. In this case, there is no need to make the illumination region of illumination light for NBI nearly coincide with that of white light, and it is only necessary that, as shown in FIG. 24, the imaging section 148B and the arrangement of individual LEDs are determined so that the illumination region of white light includes the field region of the objective optical system 123 and the illumination region of illumination light for NBI is included in both the illumination region of white light and the field region of the objective optical system 123. Here, the illumination region is defined as described below. As shown in FIG. 20, the spherical object is placed in front of the objective optical system and is illuminated by the illumination means. When the illuminance of the surface of the object is measured to find the illuminance distribution, 10% of the illuminance value at the position of the surface of the object crossing the optical axis of the objective optical system is thought of as a boundary value and a corresponding region is defined as the illumination region.

Sixth Embodiment

FIG. 27 shows the distal end of the capsule type endoscope of the sixth embodiment. In this embodiment, the shape of the transparent cover is changed, but since other features of the structure are the same as in the fourth embodiment, their explanation is omitted and like numerals are used for like members.

As shown in FIG. 27, in a transparent cover 117c, its part has a hemispherical projection. This hemispherical projection is placed so that the first lens 141 of the objective optical system 123 constituting the imaging section 148 is covered and the center of the entrance pupil of the objective optical system 123 nearly coincides with that of curvature of the hemispherical projection. By projecting the top of the objective optical system as mentioned above, the following advantage is derived. The visual field of the objective optical system 123 is not obstructed by structures placed around the imaging section 148, and the observation field with an angle of 180° C. can be ensured. In the sixth embodiment, since the imaging section 148 is constructed with the objective optical system having the observation field with an angle of 210° C., the backward view of the object becomes possible and it is avoidable to overlook the lesion in observing the inner wall of the tubular organ.

When the capsule travels through the inner wall of the tubular organ, as shown in FIG. 27, the inner wall is pushed upward by the shoulder of a transparent cover 171, and the surface of the living tissue is not brought into close contact with the projection of the transparent cover 171. Consequently, even on the periphery of the observation field, a proper distance between the projection of the transparent cover 171 and the living tissue can be ensured in order to make the observation. The capsule type endoscope of the present invention is such as to first capture and observe a lesion part in front of the observation field while traveling in the tubular organ, and then to observe this lesion part from backward. Hence, the information of the lesion part is collected from a plurality of images produced during the above process and is analyzed, and new images devoting attention to lesion parts, such as stereoscopic images and contour images, can be produced. Whereby, it is possible to make an information analysis useful for diagnosis, such as the profile analysis of the lesion part or the analysis of a distribution state.

The object-side surface of the transparent cover 171 is configured so that a portion connecting the projection and the shoulder is inclined from the center axis of the capsule toward the periphery. An illumination section 137c is placed opposite to this portion and thereby is constructed so that illumination light emitted from the light emergence surface of the white LED 151 is refracted by the inclined surface mentioned above and is spread to the periphery of the observation field. The inside surface of the transparent cover 171 can be designed so that a portion through which illumination light passes is configured into a concave shape or is replaced with a member diffusing the illumination light.

It is needless to say that the capsule type endoscope of the present invention can be designed to satisfy individual conditions described above.

Figure 28:
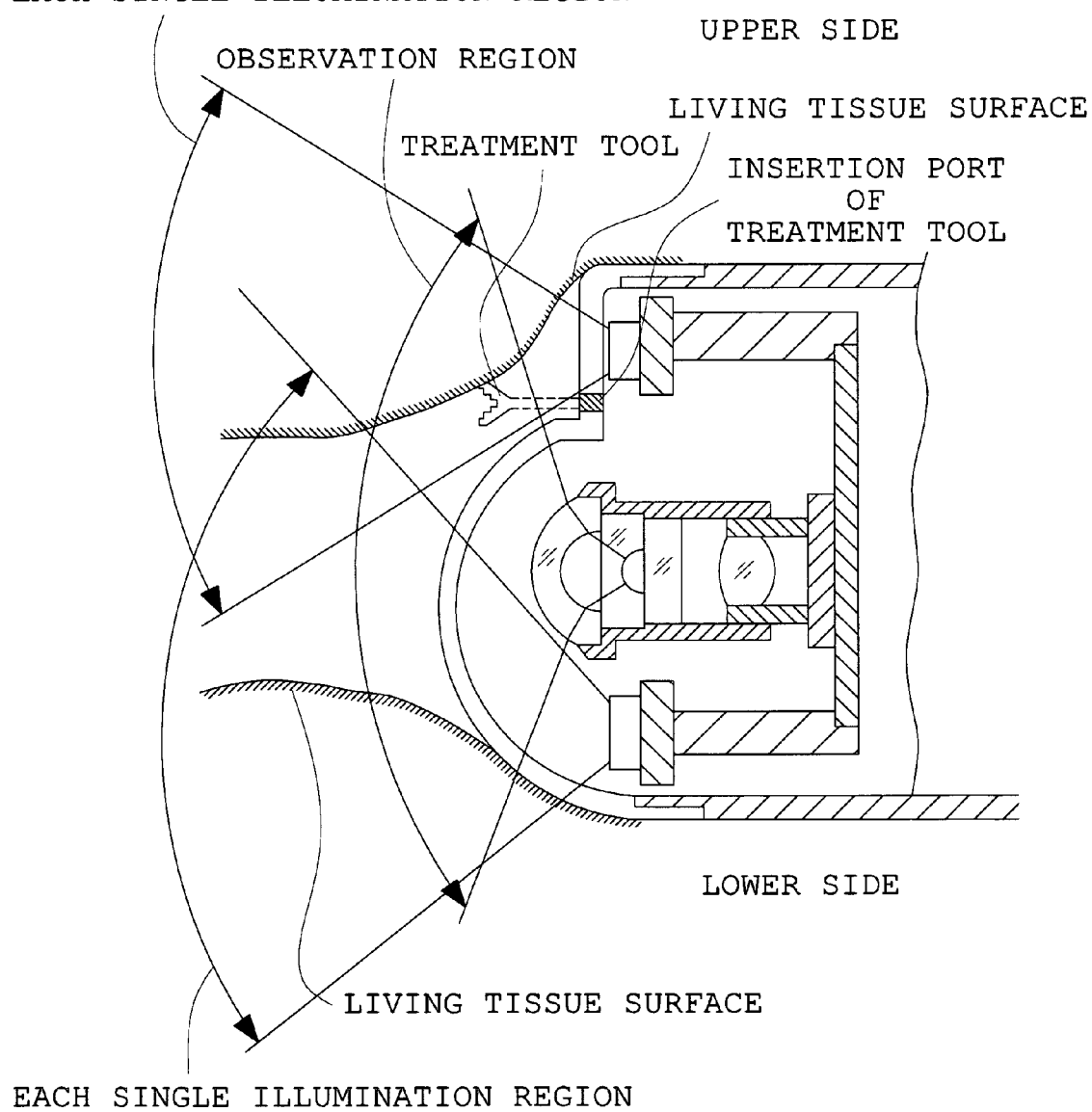
FIG. 28 is an enlarged sectional view showing the distal end of the capsule type endoscope of a modified example of the sixth embodiment.

FIG. 28 shows a modified example of the distal end of the capsule type endoscope in the sixth embodiment. In the modified example of the sixth embodiment also, the shape of the transparent cover is essential for the present invention. Since other features of the structure are the same as in the fourth embodiment, their explanation is omitted and like numerals are used for like members. This embodiment is constructed so that the shape of the transparent cover placed within the observation field of the objective optical system is different from that of the transparent cover outside the observation field. In FIG. 28, the transparent cover comes in contact with the surface of the living tissue located on the lower side and the transparent cover corresponding to a portion placed within the observation field of the objective optical system is configured into the shape of a curved surface. On the other hand, the transparent cover comes in contact with the surface of the living tissue located on the upper side and the transparent cover corresponding to a portion outside the observation field of the objective optical system is configured by combining a flat surface with a curved surface. The flat surface of the transparent cover is located perpendicular to the longitudinal center axis of the capsule and the illumination means is provided opposite to this surface. Also, an insertion port can be provided in order to insert a treatment tool from the interior toward the exterior.

Seventh Embodiment

Figure 29:
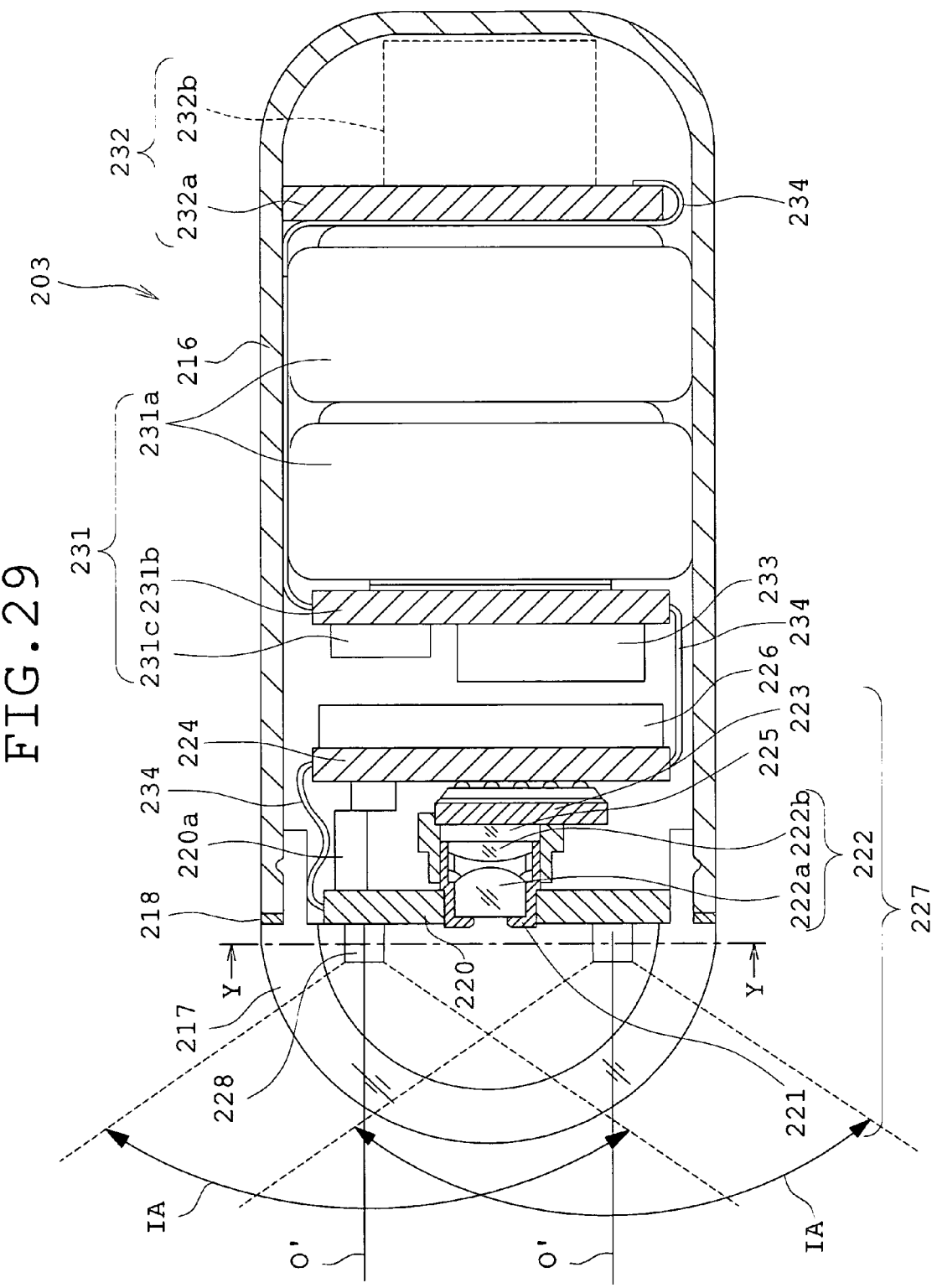
FIG. 29 is a sectional view showing the exterior structure of the capsule type endoscope of a seventh embodiment in the present invention.

FIG. 29 shows the interior structure of the capsule type endoscope of the seventh embodiment. As shown in this figure, in a capsule type endoscope 203, an outer case 216 that is cylindrical and is rounded in its rear end section and a hemispherical transparent cover 217 are connected and fixed to each other in a watertight fashion, and the interior is enclosed by a seal member 218. In the enclosed capsule vessel, built-in members described below are incorporated. Also, the outer case 216 is formed of synthetic resin, such as polysulfone or polyurethane, and the transparent cover 217 is formed of polycarbonate, cycloolefin polymer, or PMMA (polymethyl methacrylate).

An objective frame 221 is fitted into, and fixed to, an illumination substrate 220 located opposite to the transparent cover 217. In the objective frame 221, an objective optical system 222 including a first lens 222a and a second lens 222b is arranged.

At the image-forming position of the objective optical system 222, for example, a CMOS imager 223 is placed as the imaging means. The CMOS imager 223 is mounted in front of an imaging substrate 224 placed behind the illumination substrate 220. In the CMOS imager 223, its imaging surface is protected by a cover glass 225.

The imaging substrate 224 is constructed integrally with the CMOS imager 223 and the cover glass 225, and a drive control section 226 is provided on the back side of the substrate 224 so as to receive a signal from a transmitting and receiving unit provided outside the capsule to drive the CMOS imager 223 and to perform signal processing and control processing with respect to an imaging signal output from the CMOS imager 223. Also, the CMOS imager 223 and the cover glass 225 constitute an imaging section 227, together with the objective optical system 222 and the objective lens frame 221.

On the front side of the illumination substrate 220, illumination sections 228 are mounted symmetrically about the imaging section 227. Also, in the figure, O' represents the center axis (the direction of an angle of emergence of 0° C.) of the light emergence surface of each of the illumination sections 228 and IA represents the illumination region of each illumination section 228. A power source section 231 supplying the working power to individual parts is provided behind the imaging substrate 224, and a radio transmission section 232 for radio transmission to the exterior of the capsule is provided on the back side of the power source section 231.

In the power source section 231, two button-type batteries 231a are arranged as housed power sources supplying the working power in such a way that they are laminated in the axial direction of the capsule vessel. The working power of the batteries 231a can be electrically connected to a power source substrate 231b.

The power source substrate 231b is provided with an internal switch 231c including, for example, a bias magnet and a lead switch so that the on-off operation of the working power supplied from the batteries 231a is performed. On the front side of the power source substrate 231b, a recording section 233 for recording image data derived from the CMOS imager is provided.

The power source substrate 231b is connected to the imaging substrate 224 and a radio substrate 232a constituting the radio transmission section 232 through a connecting flexible substrate 234. The imaging substrate 224 is connected to the illumination substrate 220 through the connecting flexible substrate 234.

In the radio transmission section 232, the radio substrate 232a is provided with a radio antenna 232b. The radio substrate 232a has a radio transmission circuit, not shown, in which the control signal from an electric wave received by the radio antenna 232b is demodulated and output to each circuit and, for example, each of information signals of image data is modulated by the carrier wave of a preset frequency and is transmitted as the wave from the radio antenna 232b.

The illumination substrate 220 is equipped with a chip part 220a that constitutes an LED driving circuit, not shown, driving the light-emitting portion of the illumination section 228 so as to intermittently emit flash light, on the back surface of the substrate 220.

When the internal switch 231c of the power source substrate 231b is in an on state, the working power from the batteries 231a is supplied from the power source substrate 231b through the connecting flexible substrates 234 to the imaging substrate 224 and the radio substrate 232a and further to the illumination substrate 220.

In the radio transmission section 232, the radio antenna 232b receives the wave from the exterior of the capsule, and the radio transmission circuit is demodulated to output the control signals to the drive control section 226 of the imaging substrate 224 and the LED driving circuit of the illumination substrate 220.

The LED driving circuit is such as to intermittently emit flash light from the light-emitting surface of the illumination section 228. The drive control section 226 drives the CMOS imager 223 synchronously with this to capture the image of the object formed by the objective optical system 222.

The drive control section 226 serves to record image data obtained by processing the imaging signal from the CMOS imager 223 into the recording section 233. When the image data recorded into the recording section 233 reach a preset amount, the drive control section 226 reads out the image data from the recording section 233 to output the data to the radio transmission circuit of the radio transmission section 232. The radio transmission circuit of the radio transmission section 232 is such as to modulate the image data and to transmit the data as the wave from the radio antenna 232b. Also, the drive control section 226 may be designed so that the image data are not recorded into the recording section 233, but are output and transmitted directly to the radio transmission circuit.

The transmitting and receiving unit provided outside the capsule receives a signal transmitted from the capsule type endoscope 203 and stores the image data. In addition, the transmitting and receiving unit is connected to the personal computer so that stored image data are read out by the control of the personal computer and the image is displayed on the display screen of the display device.

The seventh embodiment is constructed so that the light-emitting portion emitting white light and another light-emitting portion emitting the narrow-band light are provided in the illumination section 228, from which light is emitted in turn, and reflected light from parts illuminated with light from individual light-emitting portions is imaged in turn by the imaging section 227.

Figure 30A:
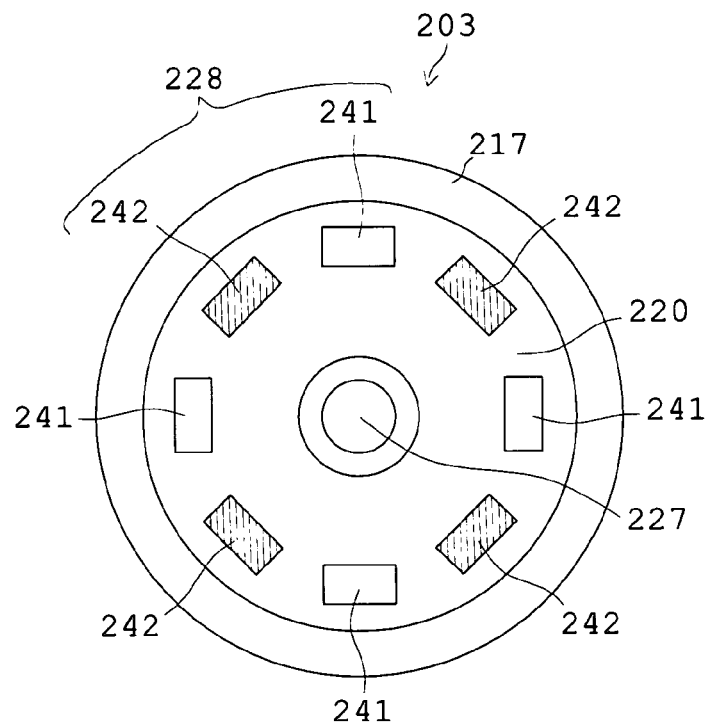
FIGS. 30A and 30B are views showing states where a light-emitting portion emitting white light is turned on and another light-emitting portion emitting narrow-band light is turned off, respectively.
Figure 30B:
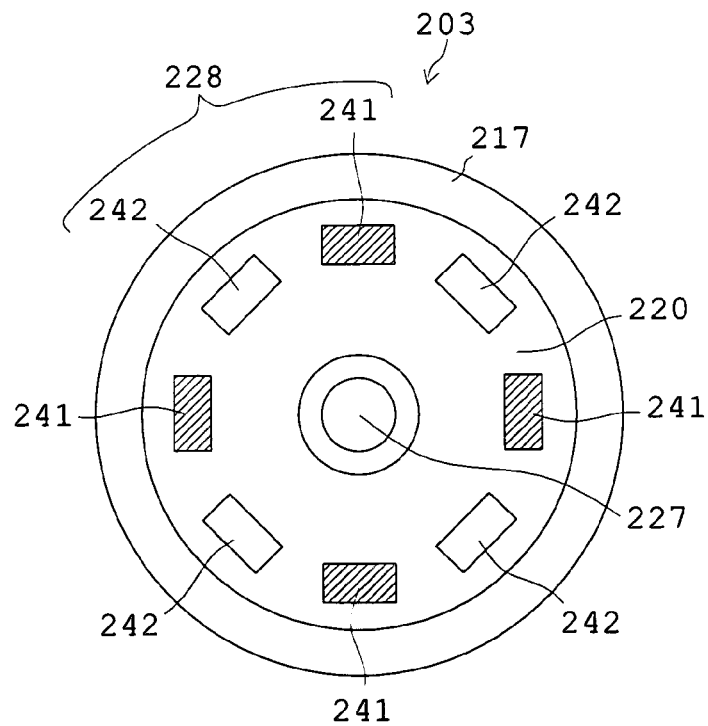

Specifically, as illustrated in FIGS. 30A and 30B, each of the illumination sections 228 is provided with a light-emitting portion 241 emitting white light and another light-emitting portion 242 emitting narrow-band light so that the illumination sections 228 surround the imaging section 227 with respect to the longitudinal center axis of the capsule. Also, FIGS. 30A and 30B are sectional views taken along line Y-Y of the capsule type endoscope in FIG. 29. FIG. 30A shows a state where the light-emitting portion 241 emitting white light is turned on and another light-emitting portion 242 emitting narrow-band light is turned off. At this time, in the capsule type endoscope, an ordinary color image is acquired. FIG. 30B shows a state where the light-emitting portion 241 emitting white light is turned off and another light-emitting portion 242 emitting narrow-band light is turned on. At this time, in the capsule type endoscope, the NBI image is acquired.

In the light-emitting portion 241, for example, a white LED emitting white light is used. On the other hand, the light-emitting portion 242 is designed as shown in FIG. 31A or 31B.

Figure 31A:
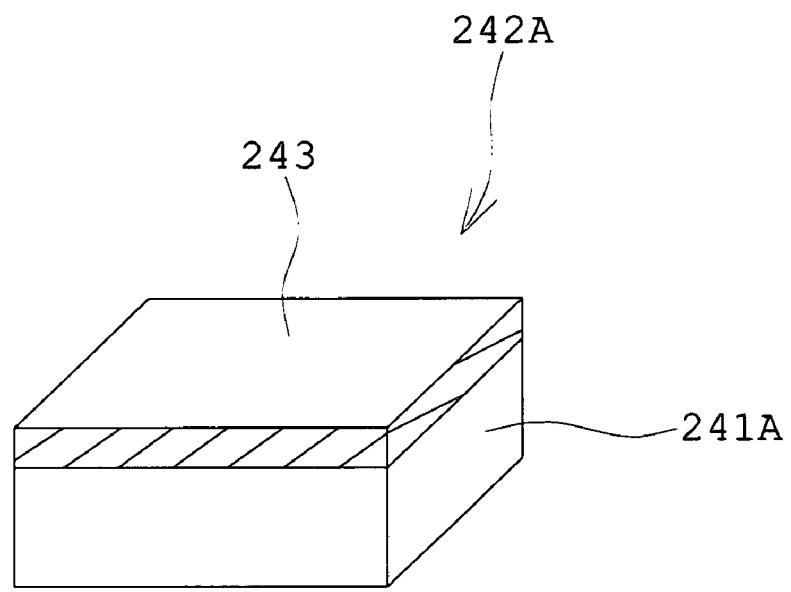
FIGS. 31A and 31B are views showing the structures of the light-emitting portions.

A light-emitting portion 242A shown in FIG. 31A is constructed so that one of the band-pass filters having transmission characteristics such as those shown in FIGS. 26A–26C is provided on the front surface of a white LED 241A. It may be constructed so that a band-pass filter having the transmission characteristic, a half-width $d \leq 30$ nm, is provided on the front surface of an LED emitting monochromatic light. A light-emitting portion 242B shown in FIG. 31B is constructed with a semiconductor laser element producing laser light with a band width of 30 nm or less.

Figure 31B:
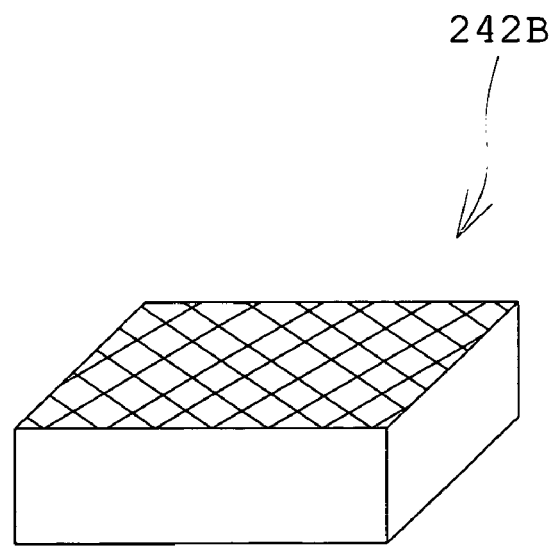

The light-emitting portions 242 (242A and 242B) emitting narrow-band light, shown in FIGS. 31A and 31B, are such as to produce, for example, red light (485–515 nm), green light (430–460 nm), and blue light (400–430 nm).

Figure 32:
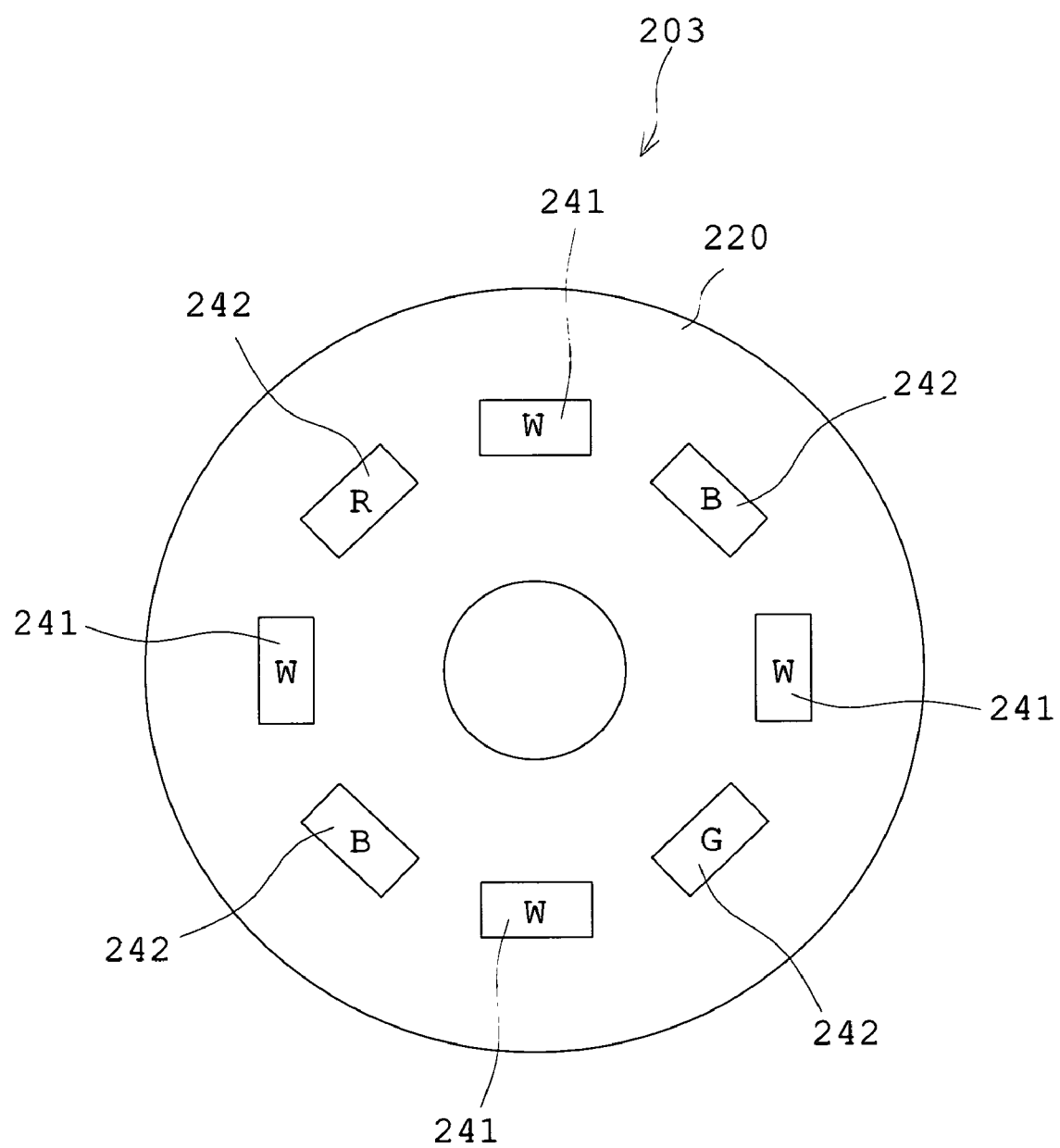
FIG. 32 is a view showing the arrangement of individual light-emitting portions.

The light-emitting portions 241 and 242, for example, as shown in FIG. 32, are designed so that the light-emitting portions for W (white), R (red), G (green), and B (blue) are arranged on the illumination substrate 220. In the arrangement example of FIG. 32, R (red), G (green), and B (blue) of the light-emitting portions 242 emitting narrow-band light are alternately arranged with respect to W (white) of the light-emitting portions 241 emitting white light to use four light-emitting portions for W (white), one light-emitting portions for R (red), one light-emitting portions for G (green), and two light-emitting portions for B (blue). Also, combinations of these light-emitting portions are arbitrarily set, according to the purpose of observation. The light-emitting portions 241 and 242 are separately controlled by the LED driving circuit, according to the purpose of observation.

The seventh embodiment is such that individual light-emitting portions are alternately arranged in a concentric manner as shown in FIGS. 30A and 30B, and thereby the illumination regions of narrow-band light and white light become nearly equal. When observations are carried out with the capsule type endoscope 203 traveling through the interior of the alimentary canal, it is necessary to find a lesion, to specify a correct position and region of the lesion, and to diagnose whether the lesion is benign or malignant while a part to be observed is within the limit of the depth of field of the objective optical system 222. The seventh embodiment is thus set so that each of the white light and the narrow-band light is emitted at least twice before the part to be observed passes the limit of the depth of field of the objective optical system 222. In this case, it is desirable that the white light and the narrow-band light are alternately emitted. For example, when narrow-band light in the blue region is used for observation, the distribution of the capillary on the surface layer of the living tissue can be depicted. In the lesion part such as a tumor, since the distribution of the capillary on the surface layer of the living tissue suffers specific degeneration, the observation with narrow-band light and the observation of the ordinary color image with white color are combined to observe the lesion, and thereby it becomes possible to accurately find a lesion that may be overlooked with only the observation of the color image.

Figure 33:
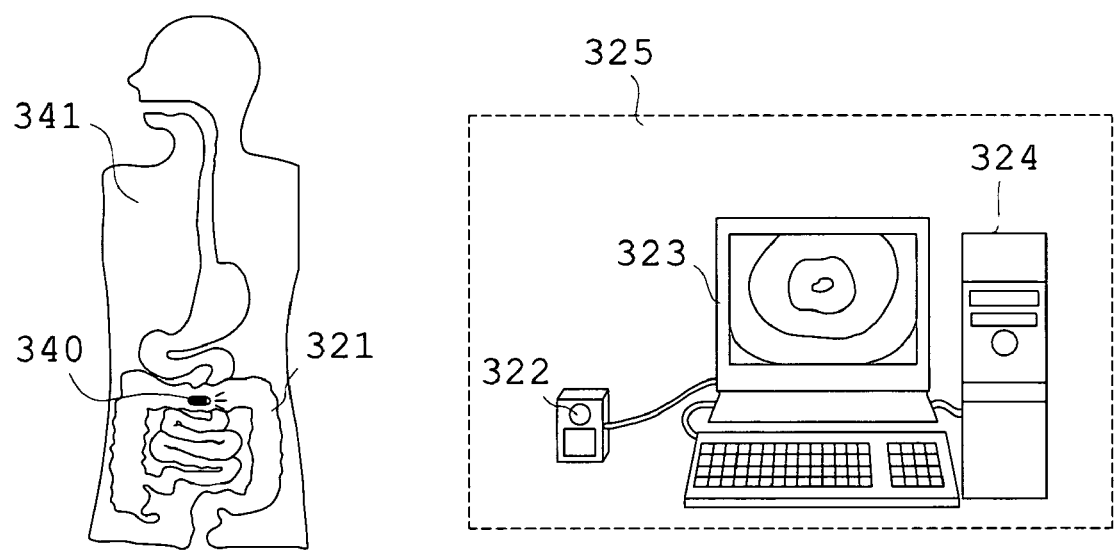
FIG. 33 is an explanatory view showing an example of a capsule type endoscope for observing the inner wall of the alimentary canal.
Figure 34:
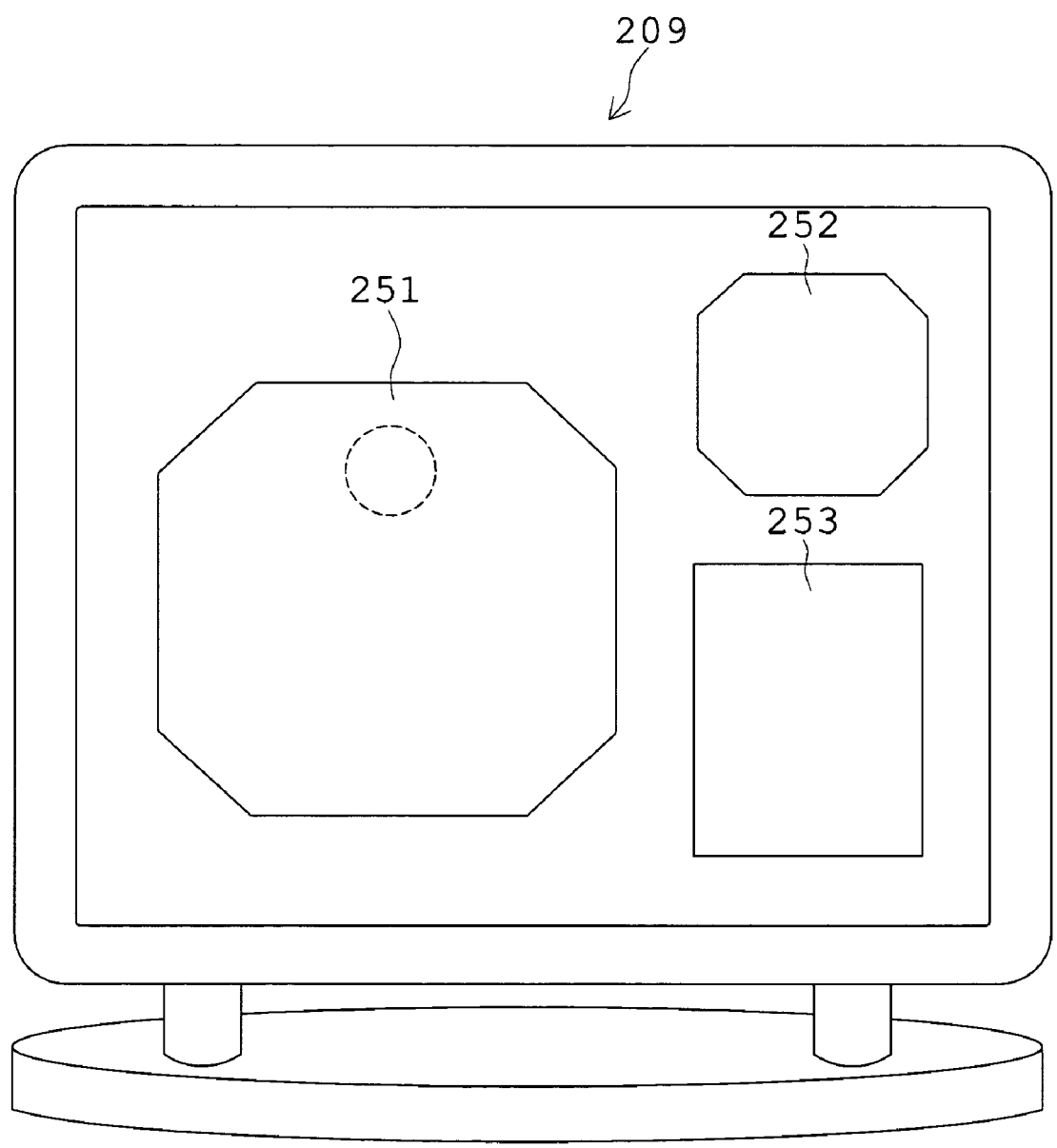
FIG. 34 is a view showing an example of image display on a monitor screen.

FIG. 33 shows an example of a capsule type endoscope for observing the inner wall of the alimentary canal. In this figure, devices surrounded by a dotted line constitute an image display system 325 provided outside the body of a patient. Although a corresponding figure is omitted for convenience, a patient 341 wears clothing considered so that the position of a capsule type endoscope 340 traveling inside the alimentary canal 321 is controlled from outside this body by a technique such as electromagnetic induction. An image signal radio-transmitted from a transmission unit housed in the capsule type endoscope 340 is received by a reception device 322 provided outside the body of the patient. The reception device 322 is connected to a personal computer 324 that is capable of processing the image signal so that an image processed by the personal computer 324 is displayed through a monitor 323. FIG. 34 shows a display example of a monitor image. As shown in FIG. 34, in the display screen of a display section 209, a display area 251 for the color image is provided in the region of a left-side middle portion, and a display area 252 for an observation image with narrow-band light is provided in a right-side upper portion. In addition, below the display area 252, an information display area 253 is provided to display information such as internal passage time and an internal position of the capsule type endoscope.

Figure 35:
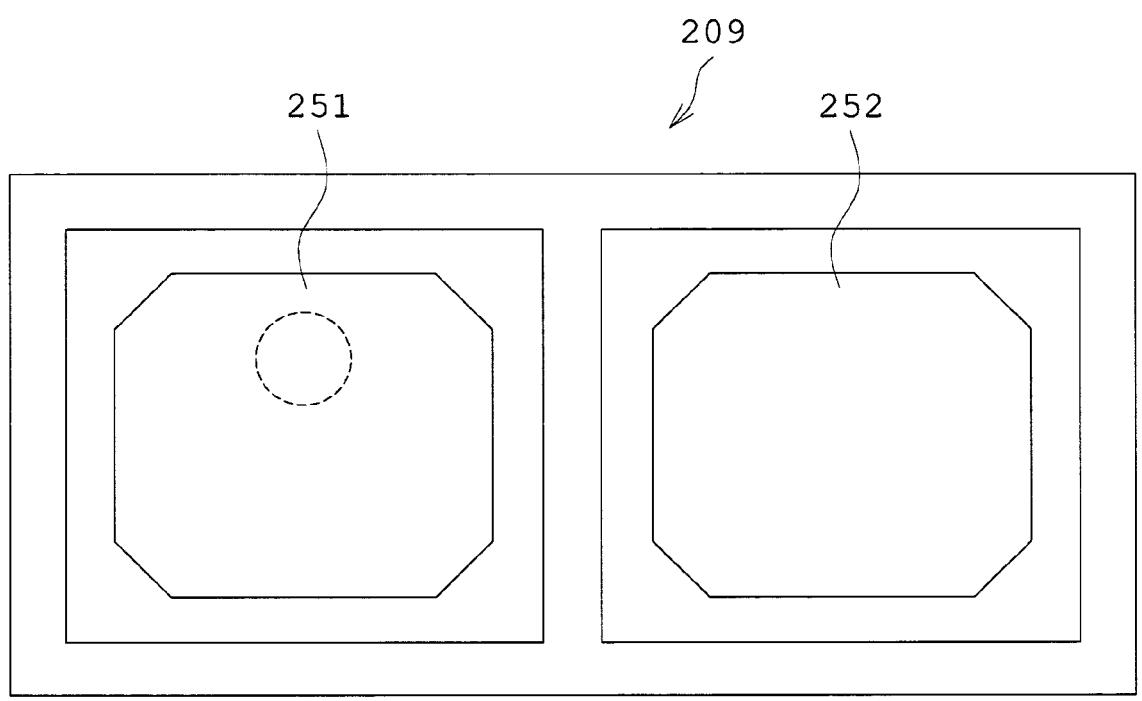
FIG. 35 is a view showing another example of image display on the monitor screen.
Figure 36A:
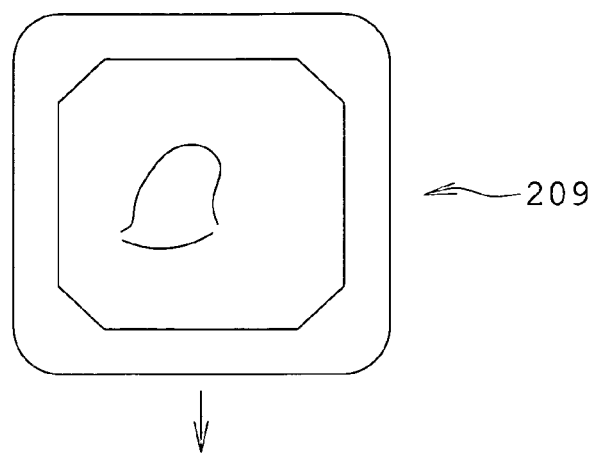
FIGS. 36A, 36B, 36C, and 36D are views showing other examples of image display on the monitor screen.
Figure 36B:
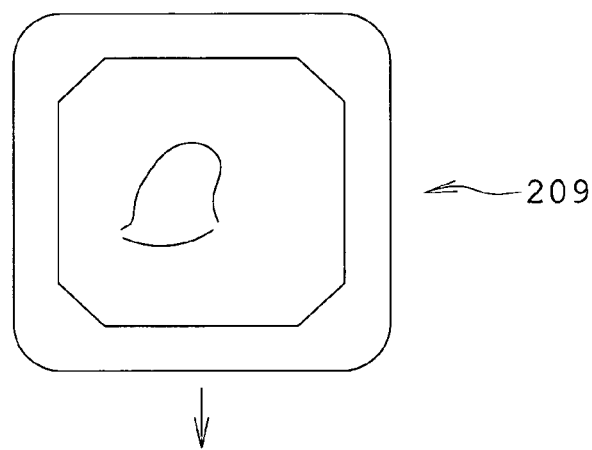
Figure 36C:
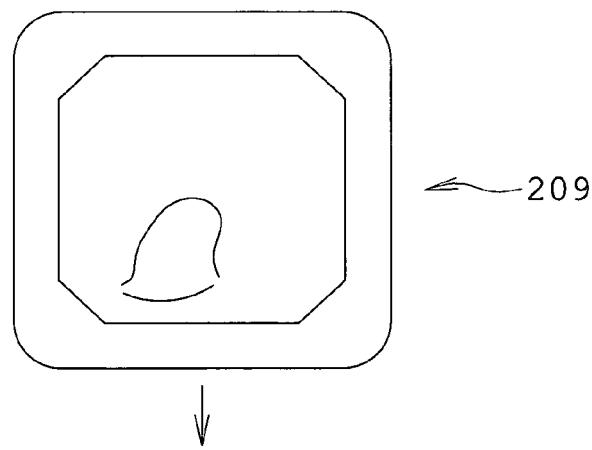
Figure 36D:
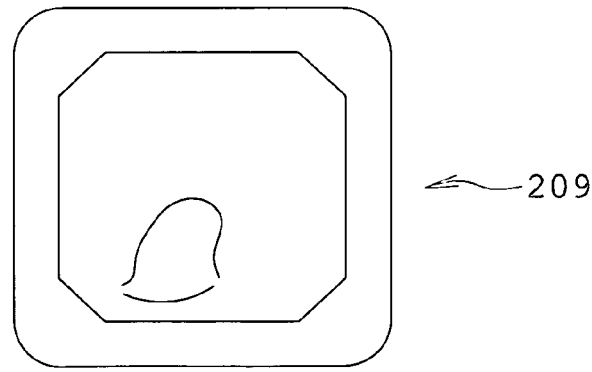

The display screen of the display section 209, for example, as shown in FIG. 35, may be constructed so that the display areas 251 and 252 are arranged on the left and right sides.

Further, the display screen of the display section 209, for example, as shown in FIGS. 36A–36D, may also be constructed so that the color image and the observation image with narrow-band light are alternately displayed.

By an image analysis circuit housed in the personal computer 324, information, such as the region, stage, and degree of malignance of the lesion, may be extracted from the observation image with narrow-band light so that the observation image is superimposed on the color image to place a false marking, or color hierarchical display is made according to the stage or level of malignance of the lesion.

Eighth Embodiment

Figure 37:
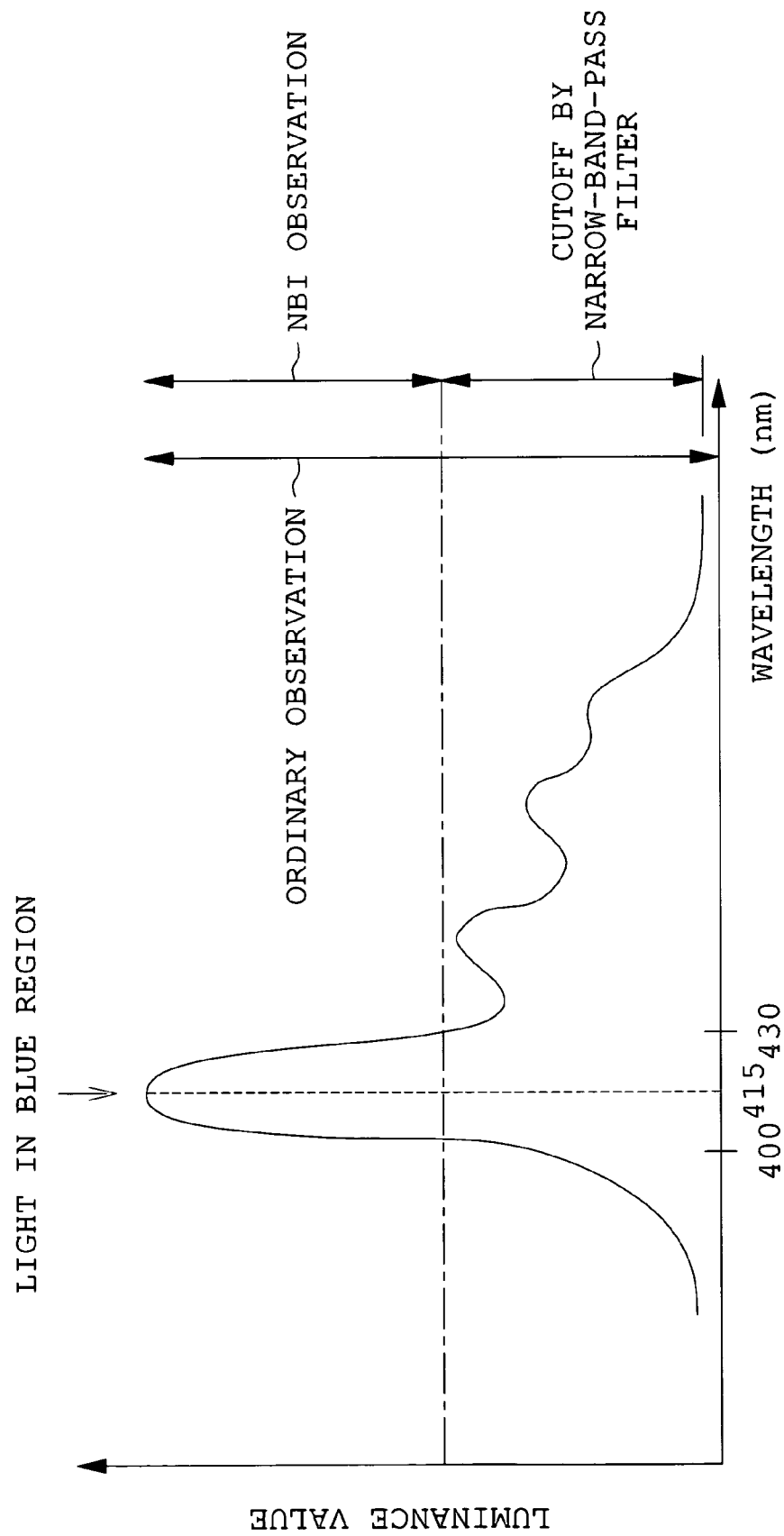
FIG. 37 is a diagram showing the spectral intensity characteristic of illumination light of a white LED used in the illumination section of the capsule type endoscope of an eighth embodiment in the present invention.
Figure 38A:
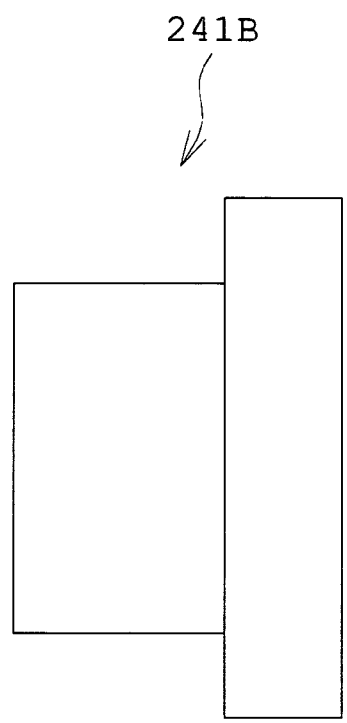
FIGS. 38A and 38B are views showing the structures of an illumination section and an imaging section, respectively, used in the capsule type endoscope of the eighth embodiment.
Figure 38B:
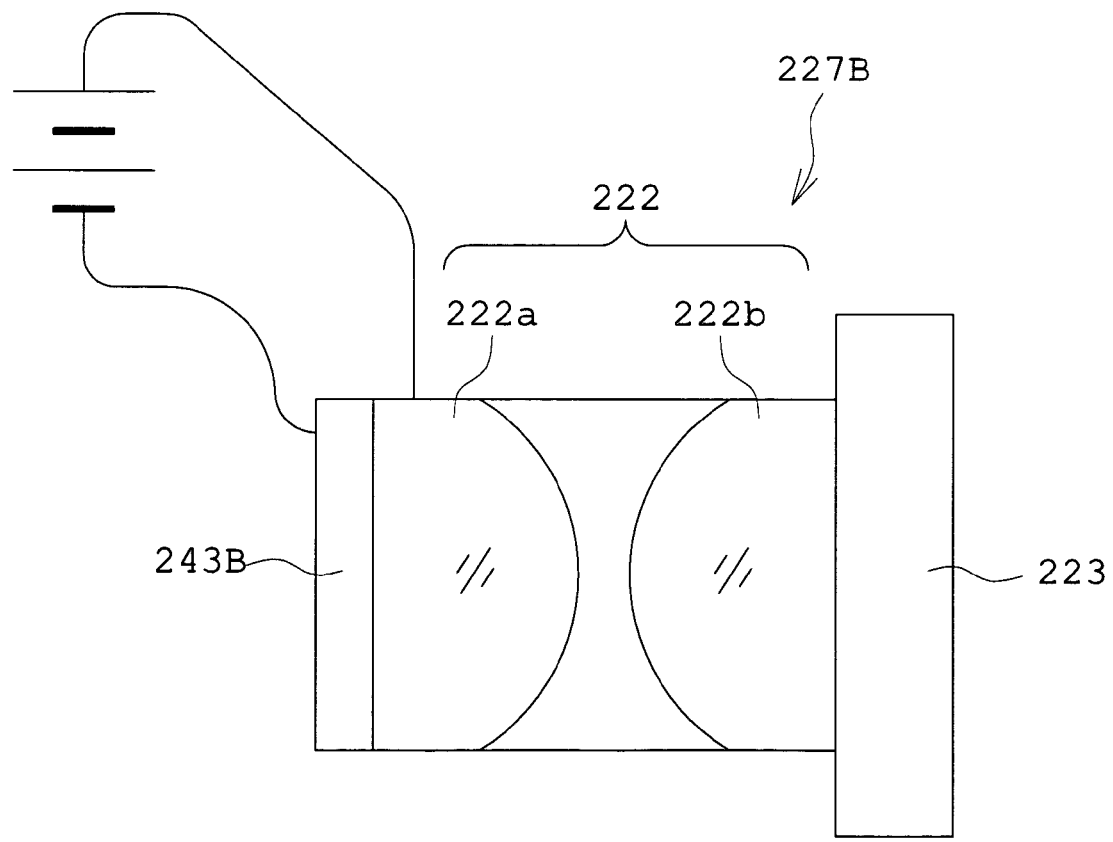

FIG. 37 shows the optical characteristic of a white LED used in the capsule type endoscope of the eighth embodiment. FIGS. 38A and 38B show the white LED having the optical characteristic of FIG. 37 and an imaging section provided with a transmission wavelength selective filter, respectively.

In the eighth embodiment, an imaging section 227B is provided with a transmission wavelength selective filter 243B selectively transmitting preset narrow-band light. Since other features of the structure are the same as in the seventh embodiment, their explanation is omitted and like numerals are used for like members. The eighth embodiment is designed to provide the illumination section 228 with a plurality of white LEDs, each having the optical characteristic such as that shown in FIG. 37.

Each of the white LEDs has a peak value at a wavelength of nearly 415 nm. In the color image observation with white light, the transmission wavelength selective filter 243B provided to the imaging section 227B is constructed to transmit reflected light from a part illuminated by the white LED. On the other hand, in the NBI observation with narrow-band light, the transmission wavelength selective filter 243B provided to the imaging section 227B is constructed to transmit only specific narrow-band light, of the reflected light from the part illuminated by the white LED. In this case also, it is desirable that the half-width d of the narrow-bang light satisfies the condition, $d \leq 30$ nm.

The transmission wavelength selective filter 243B mounted on the top side of the imaging section 227B is constructed so that the transmission wavelength can be changed by the application of voltage or electric current or by the action of electromagnetic force. For example, various devices can be used, one of which is constructed so that the on-off operation is performed with respect to the applied current, like a liquid crystal element, to thereby change the light transmission characteristic of the liquid crystal, and another is such that air space produced between substrates arranged in parallel is changed and thereby the interference action of light is utilized to change the light transmission characteristic.

An optical element in which wavelength separation is performed by the diffraction action of light, such as a hologram film, may be placed in the imaging section 227B so that an image is separated and acquired in accordance with wavelength.

A white LED 241B emits flash light through the LED driving circuit at intervals of 1–15 frames/second so that the transmission wavelength selective filter 243B changes the applied current, synchronously with the emission of flash light from the white LED 241B, through the drive control section 226. Whereby, the capsule type endoscope of the eighth embodiment is capable of bringing about the same effect as in the seventh embodiment.

Ninth Embodiment

Figure 39:
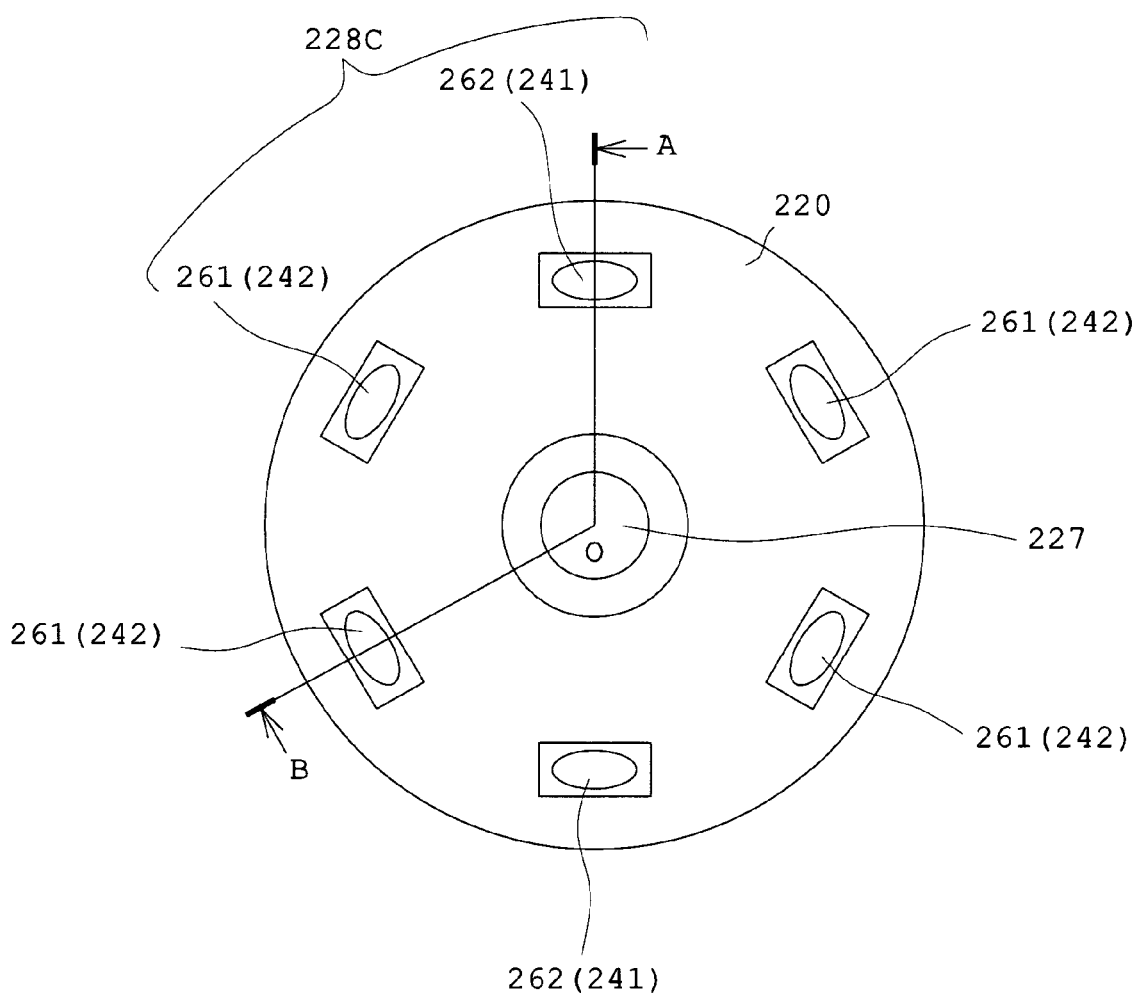
FIG. 39 is a front view showing an illumination substrate and an imaging section of the capsule type endoscope of a ninth embodiment in the present invention.
Figure 40:
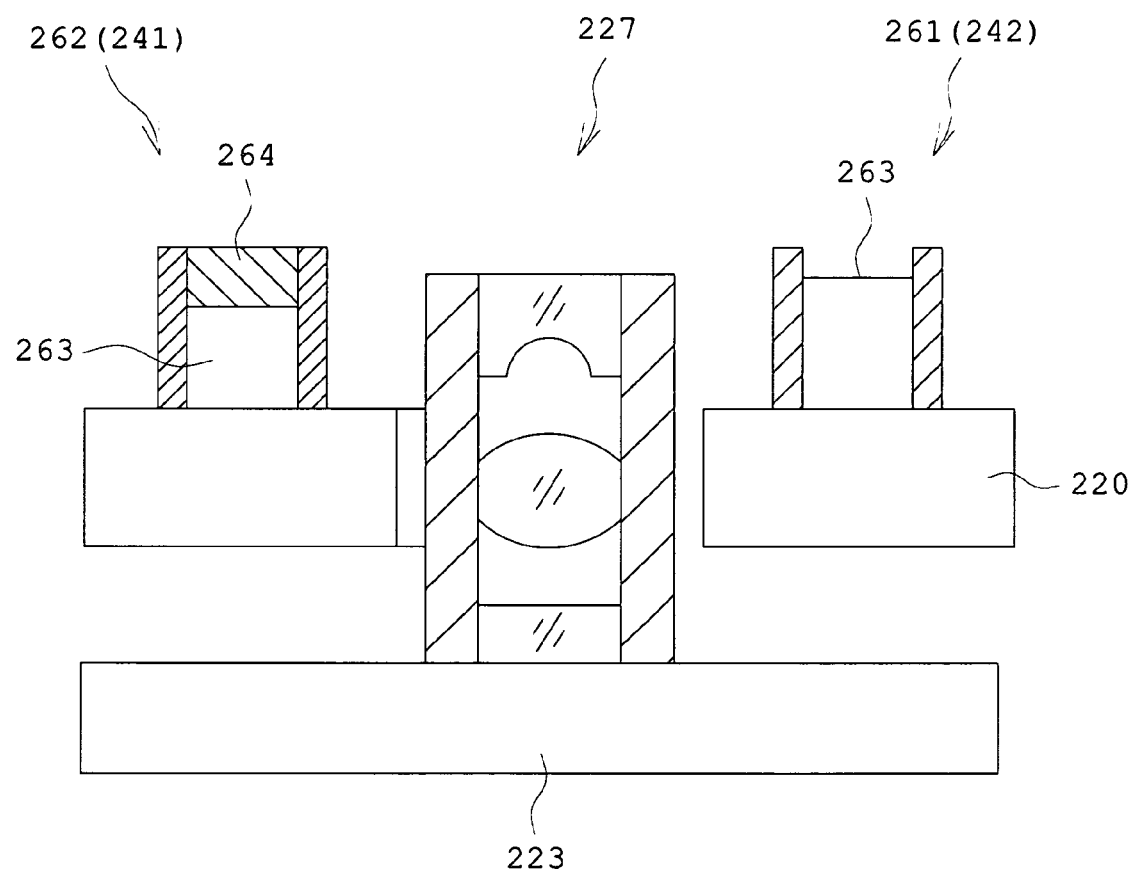
FIG. 40 is a sectional view taken along line A-O-B in FIG. 39.
Figure 41:
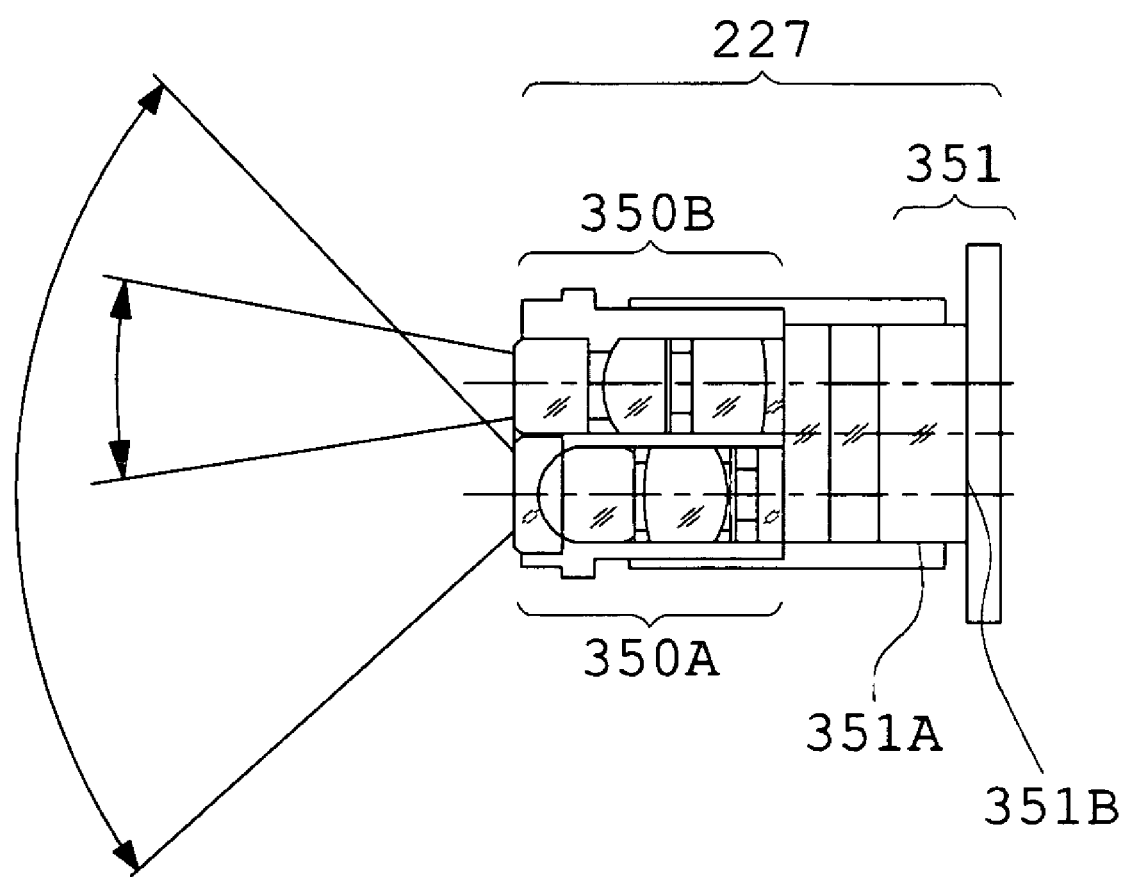
FIG. 41 is a view showing an example of the imaging section used in the capsule type endoscope of the ninth embodiment.

FIG. 39 shows an illumination substrate and an imaging section of the capsule type endoscope of the ninth embodiment. FIG. 40 is a sectional view taken along line A-O-B in FIG. 39. This embodiment is constructed so that a monochromatic LED is used as each of light-emitting portions 242 emitting narrow-band light, and a fluorescent body is provided in front of the monochromatic LED as each of the light-emitting portions 241 emitting white light to emit the white light. Since other features of the structure are the same as in the seventh embodiment, their explanation is omitted and like numerals are used for like members.

Specifically, as shown in FIG. 39, the capsule type endoscope is constructed with illumination sections 228C that include monochromatic LEDs 261 provided around the imaging section 227 and white LEDs 262 designed so that fluorescent bodies are provided in front of the monochromatic LEDs 261 to emit white light.

Each of the illumination sections 228C, as shown in FIG. 40, is provided with the white LED 262 constructed so that, for example, a blue LED 263 is placed as the monochromatic LED 261 on the illumination substrate 220 and a fluorescent body 264 is provided on the front side of the blue LED 263 to emit white light.

The imaging section 227 may also include objective units 350A and 350B constituting a twin lens reflex type. The objective unit 350A has an observation field angle of at least 100° C. to form the image of the living tissue on an imaging surface 351B of an image sensor unit 351. The objective unit 350B has an observation magnification that a close-up image of the object can be magnified two-hundredfold and displayed on the display screen of the monitor, for instance, and thus it is possible to clearly depict the pit pattern of the lesion, such as a tumor, produced in the living tissue. The observation field angle of the objective unit 350B is set to less than 60° C. and is provided so that it is included in the observation field of the objective unit 350A. In the objective unit 350B, a magnified image of the living tissue in the observation field is formed on the imaging surface 3511B of the image sensor unit 351. Also, the imaging surface 351B of the image sensor unit 351 is protected with a cover glass 351A.

According to the capsule type endoscope of the ninth embodiment, a remarkable part is determined on the basis of the image formed by the objective unit 350A having a wide-angle observation field and is magnified and imaged by the objective unit 350B, and thereby the feature of the remarkable part can be correctly held. In this case, the NBI image is acquired by the illumination of the monochromatic LED 261 and information required for the diagnosis of the part can be extracted. For example, when further detailed information is acquired on a part thought of as a lesion (which is referred to as a noticeable part) captured in the visual field of the objective unit 350A, the noticeable part is captured between the position of the far point in the depth of field of the objective unit 350A and the position of the middle point and the position of the capsule type endoscope is controlled so that the part is within the visual field of the objective unit 350B. In this case, the function of automatically performing the operation that the noticeable part is automatically tracked and introduced into the visual field of the objective unit 350B can also be imparted to the control circuit of the capsule type endoscope, housed in the personal computer. In the capsule type endoscope system provided with such a function, automatic tracking target is indicated in accordance with the operation such that an observer views the observation image displayed on the monitor and at the same time, superimposes a cursor displayed on the same image screen on the noticeable part of the observation image. Whereby, an automatic tracking function may be started. The capsule type endoscope may also be set so that when the noticeable part and the visual field of the objective unit 350B overlap on the monitor in automatic tracking, the white LEDs 262 are turned off and the monochromatic LEDs 261 are turned on.

Also, the present invention is not limited to only the embodiments mentioned above, but can be variously modified without departing from the scope and spirit of the present invention. For example, instead of using the CMOS imager, the imaging means may, of course, use a CCD imager. The number and arrangement of LEDs can be properly changed, and annular LEDs may also be used. The present invention may apply the capsule type endoscope that is provided with a plurality of imaging means and objective optical systems or is inserted through the anus and is sent back to the cecum to carry out the examination.

According to the capsule type endoscope of the present invention, as mentioned above, when the part of the cylindrical structure, such as the small intestine, is examined, favorable brightness can be obtained without causing the defect, such as halation, on the image periphery. In addition, the accuracy of diagnosis can be improved by a combination of the NBI image observation with the ordinary color image observation.

What is claimed is:

1. A capsule type endoscope comprising:
   illumination means for illuminating an object;
   imaging means for imaging the object; and
   a transparent cover for covering the illumination means and the imaging means,
   wherein the imaging means includes an objective optical system and an image sensor, and when the objective optical system satisfies Condition (1) described below and a white cylinder with a reflectance of 90%, satisfying Condition (3) described below, is observed, illuminance of an imaging surface of the image sensor satisfies Condition (2) described below, in a state where a longitudinal center axis of the capsule type endoscope coincides with a center axis of the white cylinder with a reflectance of 90%:

$$\omega \geq 50° \quad (1)$$

$$T_1 \times 0.5 \leq T_2 \quad (2)$$

$$D = 1.2 \times \Phi \quad (3)$$

where $\omega$ is a half of a field angle of the objective optical system, $T_1$ is a maximum illuminance in an area on the imaging surface of the image sensor corresponding to a field region of the objective optical system, $T_2$ is illuminance at a position on the imaging surface of the image sensor corresponding to a half of a maximum image height of the objective optical system, D is the inside diameter (mm) of the white cylinder, and Φ is the outside diameter (mm) of the capsule type endoscope.

2. A capsule type endoscope according to claim 1, wherein the objective optical system is constructed so that when a uniform surface illuminant is observed, the illuminance of the imaging surface of the image sensor at the half of the maximum image height is less than 50% of the maximum illuminance of the imaging surface of the image sensor within the field region.

3. A capsule type endoscope according to claim 2, wherein the objective optical system includes at least one aspherical lens.

4. A capsule type endoscope according to claim 1, wherein the objective optical system has a light-blocking member cutting off at least a part of a marginal light beam in a visual field.

5. A capsule type endoscope according to claim 1, wherein the illumination means includes a plurality of LEDs arranged so that center axes are inclined with respect to an optical axis of the objective optical system.

6. A capsule type endoscope according to claim 1, wherein an illumination distribution of a surface of a spherical object placed ahead of the objective optical system satisfies Condition (4) described below:

$$R(\theta) \leq R(O) \times \cos^2(\theta) \quad (4)$$

where $R(\theta)$ is illuminance of an object surface relative to a field angle $\theta°$ C. of the objective optical system, and $R(O)$ is illuminance of the object surface crossing an optical axis of the objective optical system.

* * * * *

UNITED STATES PATENT AND TRADEMARK OFFICE
CERTIFICATE OF CORRECTION

PATENT NO. : 7,153,259 B2  Page 1 of 1
APPLICATION NO. : 10/929477
DATED : December 26, 2006
INVENTOR(S) : Matsuzawa et al.

It is certified that error appears in the above-identified patent and that said Letters Patent is hereby corrected as shown below:

Column 2, line 65, change "a field angle $\theta$°C." to -- a field angle $\theta$° --;

Column 16, line 52, change "an angle of nearly 25°C." to -- an angle of nearly 25° --;

Column 17, line 38, change "at least 140°C." to -- at least 140°. --;

Column 21, line 45, change "an angle of 180°C." to -- an angle of 180° --;

Column 21, line 48, change "an angle of 210°C.," to -- an angle of 210°, --;

Column 23, line 17, change "emergence of 0°C.)" to -- emergence of 0°) --;

Column 27, line 37, change "at least 100°C." to -- at least 100° --;

Column 27, line 45, change "less than 60°C." to -- less than 60° --; and

Column 30, line 12, change "a field angle $\theta$°C." to -- a field angle $\theta$° --.

Signed and Sealed this

Twenty-sixth Day of February, 2008

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,153,259 B2 |
| APPLICATION NO. | : 10/929477 |
| DATED | : December 26, 2006 |
| INVENTOR(S) | : Matsuzawa et al. |

It is certified that error appears in the above-identified patent and that said Letters Patent is hereby corrected as shown below:

Column 2, line 65, change "a field angle $\theta$°C." to -- a field angle $\theta$° --;

Column 16, line 52, change "an angle of nearly 25°C." to -- an angle of nearly 25° --;

Column 17, line 38, change "at least 140°C." to -- at least 140°.--;

Column 21, line 45, change "an angle of 180°C." to -- an angle of 180° --;

Column 21, line 48, change "an angle of 210°C.," to -- an angle of 210°, --;

Column 23, line 17, change "emergence of 0°C.)" to -- emergence of 0°) --;

Column 27, line 37, change "at least 100°C." to -- at least 100° --;

Column 27, line 45, change "less than 60°C." to -- less than 60° --; and

Column 30, line 12, change "a field angle $\theta$°C." to -- a field angle $\theta$° --.

Signed and Sealed this

Eleventh Day of March, 2008

JON W. DUDAS
*Director of the United States Patent and Trademark Office*